(12) United States Patent
Crump et al.

(10) Patent No.: US 7,152,603 B1
(45) Date of Patent: Dec. 26, 2006

(54) ENDOTRACHEAL CATHETER AND MANIFOLD ASSEMBLY WITH IMPROVED VALVE

(75) Inventors: Chet M. Crump, Draper, UT (US); Edward B. Madsen, Riverton, UT (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/459,522

(22) Filed: Dec. 13, 1999

(51) Int. Cl.
*A61M 16/00* (2006.01)

(52) U.S. Cl. .......................... 128/207.14; 128/207.15; 128/207.16

(58) Field of Classification Search ............ 128/207.16, 128/207.14, 207.15, 205.12, 910, 911, 912
See application file for complete search history.

(56) References Cited

U.S. PATENT DOCUMENTS

| | | |
|---|---|---|
| 3,831,629 A | 8/1974 | Mackal et al. |
| 3,834,388 A | 9/1974 | Sauer |
| 3,902,500 A | 9/1975 | Dryden |
| 3,937,220 A | 2/1976 | Coyne |
| 3,991,762 A | 11/1976 | Radford |
| 4,015,336 A | 4/1977 | Johnson |
| 4,047,527 A | 9/1977 | Kelsen |
| 4,193,406 A | 3/1980 | Jinotti |
| 4,351,328 A | 9/1982 | Bodai |
| 4,468,224 A | 8/1984 | Enzmann et al. |
| 4,510,933 A | 4/1985 | Wendt et al. |
| 4,516,573 A | 5/1985 | Gedeon |
| 4,569,344 A | 2/1986 | Palmer |
| 4,573,965 A | 3/1986 | Russo |
| 4,573,979 A | 3/1986 | Blake |
| 4,574,173 A | 3/1986 | Bennett |
| 4,595,005 A | 6/1986 | Jinotti |
| 4,638,539 A | 1/1987 | Palmer |
| 4,649,913 A | 3/1987 | Watson |
| 4,657,008 A | 4/1987 | Broddner et al. |
| 4,696,305 A | 9/1987 | von Berg |
| 4,705,073 A | 11/1987 | Beck |
| 4,834,726 A | 5/1989 | Lambert |
| 4,909,248 A | 3/1990 | McLennan Anderson |

(Continued)

FOREIGN PATENT DOCUMENTS

FR    2528707    12/1983

(Continued)

OTHER PUBLICATIONS

International Search Report, Mar. 13, 2001.

(Continued)

*Primary Examiner*—Anhtuan T. Nguyen
*Assistant Examiner*—Darwin P Erezo
(74) *Attorney, Agent, or Firm*—Scott B. Garrison; William W. Letson

(57) ABSTRACT

The present invention relates to an improved flap valve or other internal component for use with respiratory suction catheter and manifold assemblies. This flap valve or other internal component provides the assembly with an improved mechanism for cleaning the tip of the catheter without drawing an excessive amount of air from the respiration circuit to which the endotracheal catheter is attached. More specifically, the present invention relates principally to a closed suction endotracheal catheter system which provides improved cleaning of the catheter while minimizing air drawn from the patient's ventilation circuit by providing at least one protrusion on at least one surface of the flap valve or other internal component. By using a flap valve or other internal component with at least one protrusion, the flap valve or other internal component is strengthened and designed to prevent the flap from scraping mucus or other secretions from the catheter onto the distal surface of the flap during retraction.

1 Claim, 15 Drawing Sheets

U.S. PATENT DOCUMENTS

| | | | |
|---|---|---|---|
| 4,929,426 | A | 5/1990 | Bodai et al. |
| 4,967,743 | A | 11/1990 | Lambert |
| D312,880 | S | 12/1990 | Bodai et al. |
| 5,060,646 | A | 10/1991 | Page |
| 5,073,164 | A | 12/1991 | Hollister et al. |
| 5,083,561 | A | 1/1992 | Russo |
| 5,088,486 | A | 2/1992 | Jinotti |
| 5,107,829 | A | 4/1992 | Lambert |
| 5,125,893 | A | 6/1992 | Dryden |
| 5,134,996 | A | 8/1992 | Bell |
| 5,139,018 | A | 8/1992 | Brodsky et al. |
| 5,140,983 | A | 8/1992 | Jinotti |
| 5,158,569 | A | 10/1992 | Strickland et al. |
| 5,184,611 | A | 2/1993 | Turnbull |
| 5,191,881 | A | 3/1993 | Beck |
| 5,213,096 | A | 5/1993 | Kihlberg et al. |
| 5,215,522 | A | 6/1993 | Page et al. |
| 5,230,332 | A | 7/1993 | Strickland |
| 5,242,084 | A | 9/1993 | Jinotti |
| 5,254,098 | A | 10/1993 | Ulrich et al. |
| 5,255,676 | A | 10/1993 | Russo |
| 5,277,177 | A | 1/1994 | Page et al. |
| 5,300,043 | A | 4/1994 | Devlin et al. |
| 5,309,902 | A | 5/1994 | Kee et al. |
| 5,309,904 | A | 5/1994 | Beck |
| 5,325,850 | A | 7/1994 | Ulrich et al. |
| 5,325,851 | A | 7/1994 | Reynolds et al. |
| 5,333,606 | A | 8/1994 | Schneider et al. |
| 5,333,607 | A | 8/1994 | Kee et al. |
| 5,337,780 | A | 8/1994 | Kee |
| 5,343,857 | A | 9/1994 | Schneider et al. |
| 5,346,478 | A | 9/1994 | Jinotti |
| 5,349,950 | A | 9/1994 | Ulrich et al. |
| 5,354,267 | A | 10/1994 | Niermann et al. |
| 5,355,876 | A | 10/1994 | Brodsky et al. |
| 5,357,946 | A | 10/1994 | Kee et al. |
| 5,368,017 | A | 11/1994 | Sorenson et al. |
| 5,370,610 | A | 12/1994 | Reynolds |
| 5,445,141 | A | 8/1995 | Kee et al. |
| 5,449,348 | A | 9/1995 | Dryden |
| 5,460,613 | A | 10/1995 | Ulrich et al. |
| 5,487,381 | A | 1/1996 | Jinotti |
| 5,490,503 | A * | 2/1996 | Hollister ............... 128/205.12 |
| 5,496,287 | A | 3/1996 | Jinotti |
| 5,513,627 | A | 5/1996 | Flam |
| 5,513,628 | A * | 5/1996 | Coles et al. ........... 128/200.26 |
| 5,578,006 | A | 11/1996 | Schön |
| 5,582,161 | A * | 12/1996 | Kee ..................... 128/200.26 |
| 5,582,165 | A | 12/1996 | Bryan et al. |
| 5,598,840 | A * | 2/1997 | Iund et al. ............. 128/207.14 |
| 5,605,149 | A | 2/1997 | Warters |
| 5,628,306 | A | 5/1997 | Kee |
| 5,642,726 | A * | 7/1997 | Owens et al. .......... 128/200.26 |
| 5,664,594 | A | 9/1997 | Kee |
| 5,676,136 | A | 10/1997 | Russo |
| 5,738,091 | A | 4/1998 | Kee et al. |
| 5,769,702 | A | 6/1998 | Hanson |
| 5,775,325 | A | 7/1998 | Russo |
| 5,791,337 | A | 8/1998 | Coles et al. |
| 5,813,402 | A | 9/1998 | Jinotti |
| 5,855,562 | A | 1/1999 | Moore et al. |
| 5,882,348 | A | 3/1999 | Winterton et al. |
| 5,919,174 | A | 7/1999 | Hanson |
| 6,070,582 | A * | 6/2000 | Kee ..................... 128/207.16 |
| 6,168,758 | B1 * | 1/2001 | Forsberg et al. .............. 422/61 |
| 6,227,200 | B1 * | 5/2001 | Crump et al. .......... 128/207.16 |

FOREIGN PATENT DOCUMENTS

| | | |
|---|---|---|
| FR | 2528707 A | 12/1983 |
| GB | 810517 | 3/1959 |
| GB | 2199630 | 7/1988 |
| GB | 2199630 A | 7/1988 |
| GB | 2199630 | 7/1998 |
| WO | 96/30069 | 10/1996 |
| WO | 9630069 | 10/1996 |
| WO | 9630069 A | 10/1996 |

OTHER PUBLICATIONS

International Search Report, Mar. 20, 2001.
U.S. Appl. No. 09/471,317, filed Dec. 23, 1999.
U.S. Appl. No. 09/460,257, filed Dec. 13, 1999.
U.S. Appl. No. 09/716,486, filed Nov. 20, 2000.
U.S. Appl. No. 09/693,261, filed Oct. 20, 2000.
U.S. Appl. No. 09/357,591, filed Jul. 20, 1999.

* cited by examiner

ENDOTRACHEAL CATHETER AND MANIFOLD ASSEMBLY WITH IMPROVED VALVE

FIELD OF THE INVENTION

The present invention relates to an improved flap valve or other internal component for use with respiratory suction catheter and manifold assemblies by providing at least one protrusion on at least one surface of the flap valve or other internal component that may aid in reducing or preventing mucus and similar secretions from collecting on the distal surface of the flap valve or other internal component during retraction of the catheter, thus improving the cleaning of the assembly.

BACKGROUND OF THE INVENTION

In the past twenty years, the medical industry has seen an increased interest in closed suction catheter systems to create artificial airways. Such systems were disclosed in U.S. Pat. No. 3,991,762 ("Radford"), which provided for a catheter within a protective sleeve such that the catheter is only advanced when suctioning is desired. Furthermore, U.S. Pat. No. 4,569,344 ("Palmer"), offered an improved system to reduce the risk of cross-contamination between the patient and the medical personnel using the device. More recently, interest has developed in catheter systems having a flap valve by which the internal passageway of the catheter can be closed off from the manifold.

There are a variety of different circumstances for which a person may be required to have an artificial airway, such as an endotracheal catheter tube, placed in his respiratory system. In some circumstances, such as surgery, the artificial airway's function is primarily to keep the patient's airway open so that adequate lung ventilation can be maintained during the procedure.

Moreover, because the endotracheal tube may be left in the patient for a prolonged period of time, it will become necessary to service these endotracheal catheter tube and manifold assemblies to replace, repair, refit, or otherwise manipulate the assembly. Because patients may need the use of an endotracheal tube to sustain mechanical ventilation for the life of the patient to remove respiratory secretions periodically, it is very useful for the assembly to comprise flap valves and other internal components that aid in the cleaning of the assembly.

In practice, a respiratory suction catheter is advanced through the inner passageway of the catheter and manifold assembly. As the suction catheter is withdrawn, a negative pressure is applied to the interior of the assembly to draw mucus and other secretions from the patient's respiratory system. While a substantial amount of the mucus and other secretions may be withdrawn through the catheter, a portion of the mucus and other secretions remain on the outside of the catheter. Because patient secretions can contain infectious agents, such as streptococcus, pseudomonas, staphylococcus and even HIV, it is important to shield clinicians from contact with the catheter. Likewise, it is important to shield patients' from communicable pathogens in the environment and those that may be carried by the clinician. This is particularly important because patients on mechanical ventilation often have compromised immune systems. Therefore there exists a need to form the internal components of the assembly such as the flap valve such that the withdrawal or retraction of the catheter does not coat the internal components such as a flap valve with mucus and similar secretions such the that cleaning of the assembly is impeded.

SUMMARY OF THE INVENTION

The present invention provides an improved design for internal components for the catheter tube manifold assemblies, including the flap valve of respiratory suction catheter assemblies. The flap valve or other internal component is preferably formed with at least one protrusion on at least one surface such that each protrusion will aid in the positioning of the flap valve or other internal component. By forming the flap valve or other internal component with at least one protrusion sufficient to maintain a space between the flap valve and the distal portion of a catheter that may translate within the assembly, the integrity and working condition of the flap valve or other internal component is protected while improving the cleaning of the assembly. This improved flap valve or other internal component will minimize the amount of mucus and similar secretions that collects or coats the distal surface of the flap valve during retraction or withdrawal of the catheter from the assembly and thus improves removal of mucus and other secretions from the distal tip of the catheter. By automatically separating or otherwise partitioning at least a portion of the assembly to form a cleaning area from the ventilation circuit, each protrusion formed or otherwise attached to the flap valve or other internal component will cause a more efficient cleaning to be affected by ensuring that the majority of the mucus or similar secretions are withdrawn with the catheter into this cleaning area.

Various of the above and other objects of the invention are realized in specific illustrated embodiments of an improved respiratory suction catheter apparatus set forth more fully herein and claimed below. The embodiments of an improved respiratory suction catheter apparatus typically include a manifold for attachment to an artificial airway, such as an endotracheal tube, to form a ventilation circuit, a catheter which is displaceable through the manifold and into the artificial airway to suction secretions from the artificial airway and lungs, and a variation of the flap valve or other internal component valve mechanism of the present invention disposed adjacent the ventilation circuit to minimize the air drawn from the ventilation circuit of a patient while the catheter is being cleaned.

In accordance with one aspect of the invention, the flap valve or other internal component valve mechanism is configured to engage the catheter as it is withdrawn through the manifold to thereby minimize the amount of mucus and similar secretions that may otherwise be scraped onto a distal surface of the flap valve. This flap valve may be configured to lock in a closed position when it is pulled toward the withdrawn catheter to thereby maintain a selective isolation or separation between the catheter tip and the airway through the manifold. Using an air makeup, to allow makeup air into the catheter and thereby ensure proper evacuation of secretions and any liquid used to clean the assembly, may enhance this flap valve or other internal component.

In a preferred embodiment of the present invention, each protrusion may be connected by a bridge that improves the interaction between the translating catheter and the protrusion formed on flap valve such that withdrawal or retraction of the catheter does not cause mucus or similar secretions from being scraped onto the flap valve in a manner that impedes cleaning of the assembly.

BRIEF DESCRIPTION OF THE DRAWINGS

The above and other objects, features and advantages of the invention will become apparent from a consideration of the following detailed description presented in connection with the accompanying drawings in which:

FIG. 4C shows a fragmented, cross-sectional view of the embodiment of FIGS. 4A and 4B, with an air makeup mechanism in an open position to facilitate suctioning of mucus and the like;

DETAILED DESCRIPTION OF THE PREFERRED EMBODIMENTS

Figure 1:
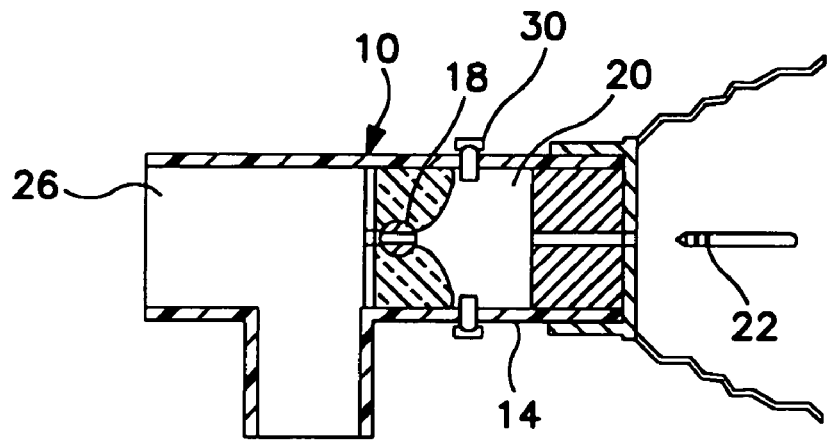
FIG. 1 shows a cross-sectional view of a manifold and catheter cleansing mechanism the prior art.

Reference will now be made to the drawings in which the various elements of the present invention will be given numeral designations wherein like numerals are used to designate like materials throughout. It is to be understood that the following description is only exemplary of the principles of the present invention, and should not be viewed as narrowing the pending claims. Those skilled in the art will appreciate that aspects of the various embodiments discussed may be interchanged and modified without departing from the scope and spirit of the invention. Moreover, the use of reference numerals in each Figure is only to show a preferred embodiment of the corresponding structure and is not intended to limit the scope of the invention as claimed herein.

Referring to FIG. 1, there is shown a cross-sectional view of a manifold 10 and catheter cleansing mechanism 14 in accordance with the teachings of the prior art. The manifold has a valve mechanism in the form of a rotatable rod 18 for selectively isolating a lavage chamber 20 from the ventilation circuit 26. When the distal end of the catheter 22 is disposed in the lavage chamber 20, a lavage solution can be injected through a side port 30 to help wash the mucus and other secretions from the exterior of the catheter 22. Because of the relative size and dimensions of the lavage chamber 20, however, there is nothing to force vigorous interaction between the lavage solution and the secretions on the exterior of the catheter. Additionally, because the lavage chamber is not configured for makeup air to enter when the rotatable rod 18 is closed, a vacuum can be created in the lavage chamber 20 that interferes with effective suctioning.

An additional disadvantage of the embodiment shown in FIG. 1 is that the closure mechanism for such devices typically must be manually activated. If the user fails to close the rotatable rod 18, actuation of suction through the catheter will draw air from the ventilation circuit 26.

Figure 2:
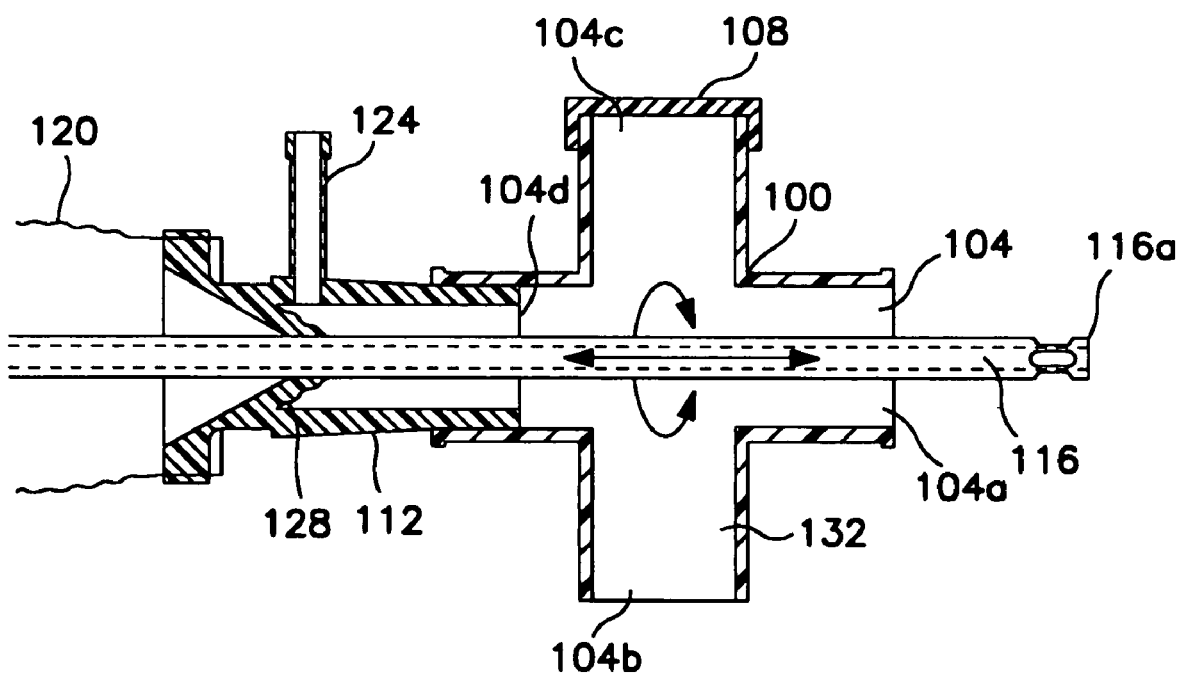
FIG. 2 shows a cross-sectional view of another manifold and catheter cleaning mechanism in the prior art.

Turning now to FIG. 2, there is shown a cross-sectional view of an alternative embodiment of the prior art. The manifold 100 is provided with a plurality of ports 104. A first port 104a is attached to the hub of an endotracheal tube of the patient to conduct respiratory air to and from the endotracheal tube.

Thus the manifold forms part of a ventilation circuit. The air is typically provided to and removed from the manifold through a second port 104b which is attached to a pair of ventilation tubes via a connector (not shown). The ventilation tubes are, in turn, connected to a mechanical ventilator (not shown) in a manner that will be well known to those skilled in the art.

A third port 104c is provided opposite the second port 104b. The third port 104c is typically covered with a cap 108 which is removed when "blow-by" is desired to wean a patient from forced ventilation.

The manifold also has a fourth port 104d. A coupling 112 is configured to form a force-fit engagement with the fourth port 104d and effectively connects the catheter 116 and a protective sleeve 120 to the manifold 100. Disposed adjacent a proximal end of the coupling 112 is a lavage port 124 through which a cleaning liquid can be injected to rinse the exterior of the catheter 116. Such a configuration is advantageous because the lavage port 124 is positioned adjacent a seal 128 which is configured to wipe mucus and other secretions from the catheter 116 as is drawn through the seal. Thus, a user will typically withdraw the catheter 116 until the distal end 116a thereof is positioned slightly distally of the seal 128, and then the cleaning solution will be injected into the lavage port 124 to assist in the removal of secretions. While such a method of removing the secretions is generally effective, it can draw more air from the ventilation circuit 132 than is necessary to effectively clean the distal end 116a of the catheter 116. Additionally, it is common for respiratory therapists and other clinicians to maintain the suction on as the distal end 116a of the catheter 116 is drawn from the first port 104a to a position immediately adjacent the seal 128.

Figure 3A:
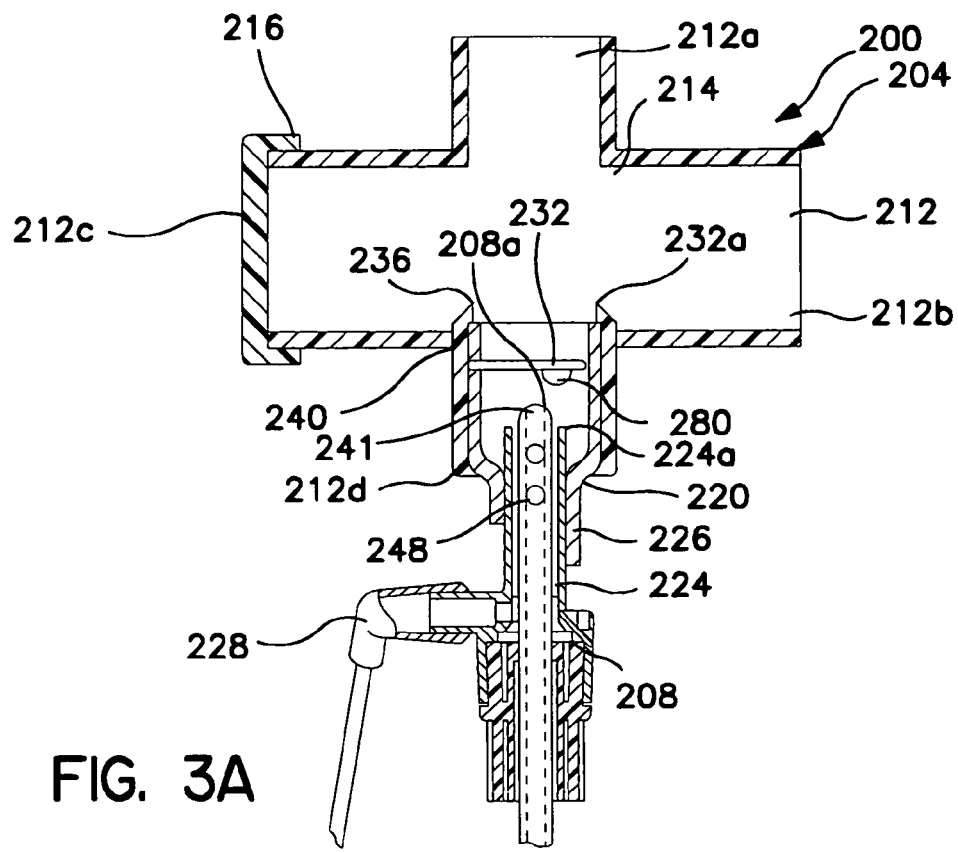
FIG. 3A shows a cross-sectional view of the manifold and distal portion of a catheter of an improved respiratory suction catheter apparatus with the improved valve in an open position in accordance with the principles of the present invention.

Turning now to FIG. 3A, there is shown a cross-sectional view of a portion of an improved endotracheal catheter, generally indicated at 200. The endotracheal catheter includes a manifold, generally indicated at 204 and a catheter 208. The manifold 204 includes a plurality of ports 212a–c. A first port 212a is configured for attachment to the proximal end of an artificial airway, such as the hub of an endotracheal tube, tracheostomy tube, etc. A second port 212b is typically connected to a pair of ventilator tubes (not shown) by means of an adapter (not shown), in accordance with common practice in the art.

As used herein, distal refers generally to the direction of the patient, while proximal refers to the direction of the clinician. Unless otherwise noted, the drawings of FIG. 2A are oriented such that the distal (patient) end is toward the top of the page, while the proximal (clinician) end is toward the bottom of the page.

During normal usage, conditioned inspiratory air is forced through one of the ventilator tubes, through the second port 212b and the first port 212a and into the patient's lungs via the artificial airway. Exhaled air is carried through the first port 212a and then the second port 212b and out through the other ventilator tube. Thus, the manifold 204 forms part of a ventilation circuit 214 through which respiratory air is cycled.

Also forming part of the manifold 204 is a third port 212c. A cap 216 typically covers the third port 212c. Whenever mechanical ventilation is used, it is the goal to someday return the patient to voluntary or spontaneous breathing. To accomplish this, the patient must usually be weaned from the mechanical ventilation—to spontaneous breathing. To this end, the cap 216 may be removed from the third port 212c so that oxygenated air is passed by the patient's endotracheal tube, but inspiratory air is not forced into the patient's lungs by means of a totally closed circuit. This arrangement commonly called "blow-by," enables the patient to gradually resume natural or spontaneous breathing.

The manifold 204 also has a fourth port 212d. The fourth port 212d is disposed generally opposite the first port 212a and is configured to allow the catheter 208 to slide therethrough and into the first port to enable suctioning of the patient. At the completion of suctioning, the catheter 208 is pulled back into the fourth port 212d to prevent interference with the ventilation circuit 214.

Disposed between the wall forming the fourth port 212d and the catheter 208 is a coupling or adapter 220. On an outer extreme, the adapter 220 engages the wall defining the fourth port 212d. On an inner extreme, the adapter 220 engages a collar 224 that closely surrounds the catheter 208 so as to leave a small cylindrical space 226 around the catheter 208. Ideally the space between the catheter 208 and the collar 224 is between about 0.127 mm (0.005 inches) and about 0.381 mm (0.015 inches). This proximity provides two important advantages. First, if lavage needs to be provided to the lungs of the patient, injecting lavage solution through the lavage port 228 and into the cylindrical space 226 causes a stream of lavage solution to be directed out the distal end 224a of the collar and through the first port 212a. If the spacing between the catheter 208 and the collar 224 is too large the lavage solution cannot be thus directed. Second, as the catheter 208 is drawn back into the collar 224 after use, the collar helps to wipe any heavy layers of mucus or other secretions from the outside of the catheter.

Injecting sterile saline or cleaning solution through the lavage port 228 further removes the secretions from the exterior of the catheter 208 and enhances evacuation by suction in the catheter. This configuration also minimizes the volumes of air and cleaning solution necessary to effect cleaning.

While the collar 224 configuration shown in FIG. 3A is beneficial, it is still common to have secretions build up on the distal end 208a of the catheter 208. If such build up is not promptly removed, it can interfere with the ability of the catheter to properly suction the patient. It can also serve as a culture medium for pathogens within the closed suction catheter system.

As shown in FIG. 3A, a flap valve 232 is hingedly attached to an annular ring 236 disposed inside the fourth port 212d so as to enable the flap valve 232 to pivot with respect to the ring to form a self-closing valve member. Of course, the flap valve 232 could be attached directly to the wall of the manifold 204 defining the fourth port 212d or to the adapter 220. The hinged attachment 240 allows the flap valve 232 to selectively move while maintaining alignment with the catheter tip, thereby creating a self-closing flap valve. Moreover, during retraction or withdrawal of catheter 208, mucus and similar secretions may be scraped from the catheter 208 and collect in areas that are difficult to clean. For example, these secretions may collect on the distal surface of the flap valve 232 that is discussed below. As shown in FIG. 3A, valve 232 further comprises at least one non-planer, outward extruding protrusion 280 on at least one surface of flap 232. As shown, each protrusion 280 on flap 232 may be attached or otherwise secured to flap 232. Preferably, each protrusion 280 is formed on at least one surface of flap 232 during the formation of flap 232. At least one protrusion 280 extends from the proximal surface of flap 232 and is positioned such that the catheter 208 contacts at least one protrusion 280 rather than the proximal surface of flap valve 232.

Figure 3B:
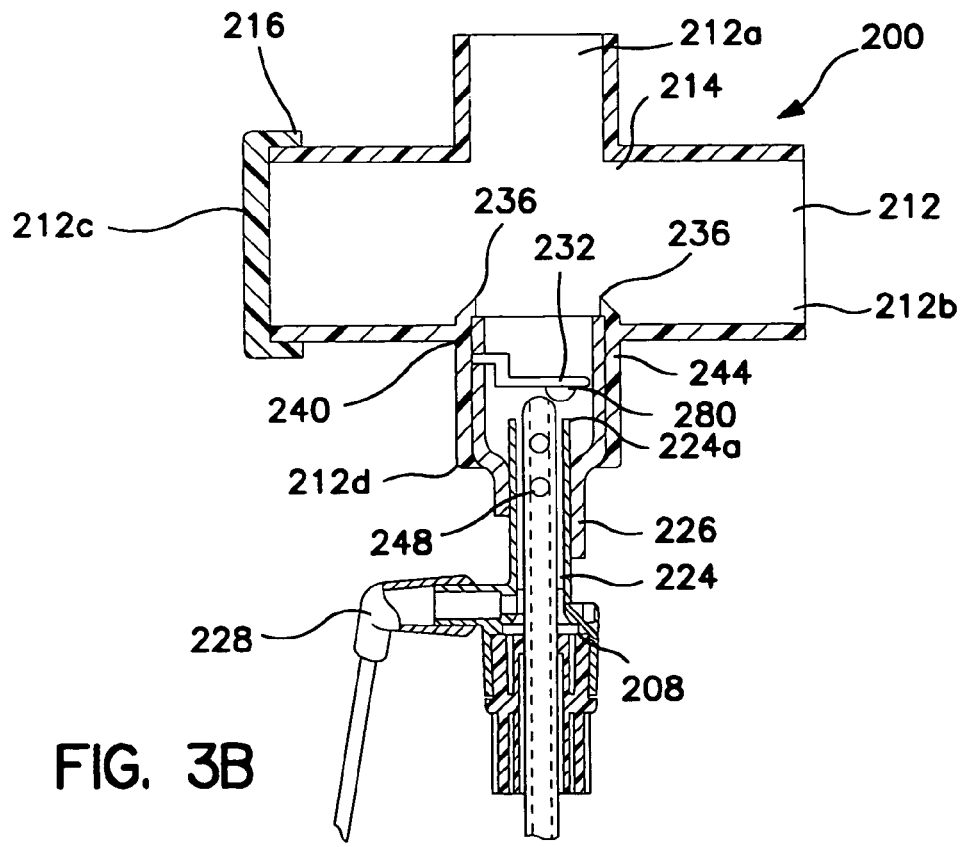
FIG. 3B shows a cross-sectional view of the manifold and catheter portion shown in FIG. 3A, with the improved valve in a second, nearly closed position.

As shown in FIG. 3B, the flap valve 232 is positioned to align with the distal end 208a of the catheter 208 when the catheter is almost completely withdrawn into the collar 224. The hinged attachment 240 is sufficiently flexible that suction through the distal end 208a of the catheter 208 will draw the flap valve 232 proximally from a first, distal position into a second, proximal position, wherein the flap valve contacts with the distal end of the catheter 208. Thus, the flap valve 232 and related structures form a self-closing valve wherein no additional external manipulation of the catheter system is needed to close the valve 232. As with most closed suction catheters, the catheter 208 is formed such that a primary aperture 244 is formed in the distal end 208a and one or more lateral apertures 248 positioned slightly proximal from the distal end may also be formed therein.

As the distal end of catheter 208 approaches flap 232, the distal end of catheter 208 will contact that flap 232. In this arrangement, the proximity to flap 232 substantially reduces the rate of suction through catheter tip aperture 244. This decrease in suction at aperture 244 effectively increases suction flow in lateral apertures 248, thereby increasing the ability of lateral apertures 248 to evacuate any secretions contained between the outside of catheter 208 and the interior collar 244.

Because the lateral apertures 248 are generally smaller than the distal aperture 244 and because airflow to the lateral apertures 248 is limited by the collar 224, the catheter 208 will increase the evacuation of secretions between the outside of catheter 208 in the interior of the collar 244 while not significantly taxing the airflow in the ventilation circuit.

As shown in FIGS. 3A and 3B, the proximal surface 232a (i.e., the side opposite the ventilation circuit 214) of the flap valve 232 is generally planar. At least one raised protrusion 280 on flap valve 232 extends proximally from this plane. As shown, a single protrusion 280 remains dormant until the catheter 208 translates through flap valve 232 during insertion or retraction periods.

Figure 3C:
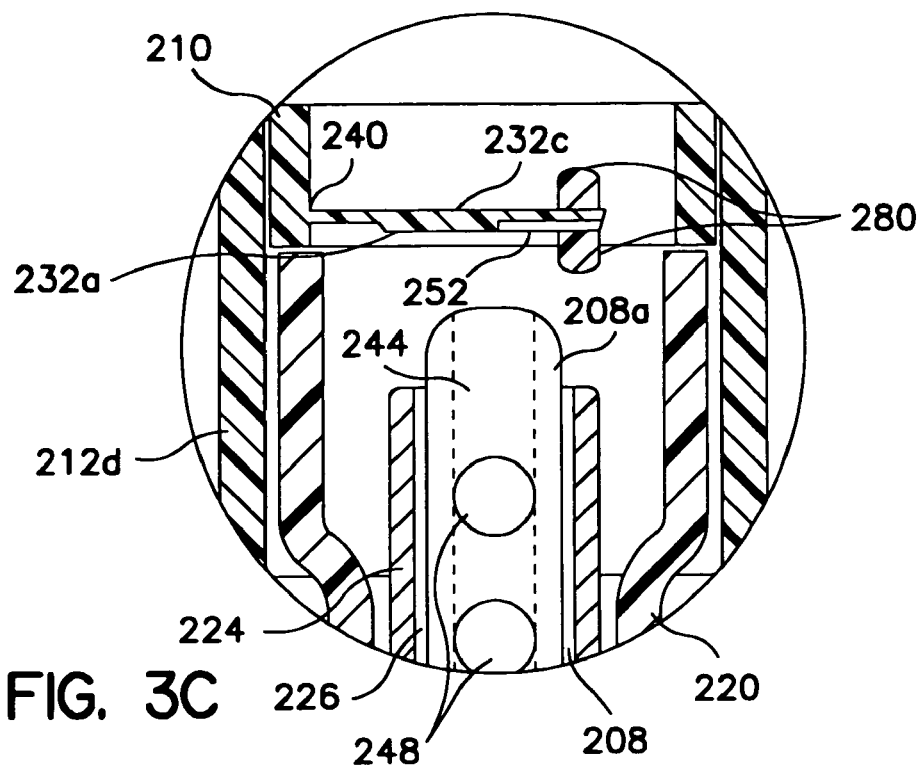
FIG. 3C shows a fragmented, close-up cross-sectional view of one embodiment of the improved respiratory suction catheter apparatus shown in FIG. 3A.

Turning now to FIG. 3C, there is shown a close-up cross-sectional view of the embodiment shown in FIGS. 3A and 3B with a slight modification to the flap valve 232. Unlike the flap valve 232 in FIGS. 3A and 3B which is substantially planar save each protrusion 280 formed or otherwise attached thereto, the flap valve 232 in FIG. 3C further comprises a channel 252 formed therein on the proximal surface 232a. The channel 252, prevents the flap valve 232 from forming a sealing engagement with the distal end 208a of the catheter 208. The channel 252 ensures that a controlled rate of airflow may be drawn into the aperture 244 at the distal most end 208 of the catheter.

The measured volume of air is drawn in through the channel 252 can have an important effect. Specifically, the air increases turbulent airflow both within the catheter 208 and immediately around its exterior. The turbulent airflow in turn, assists in breaking up agglomerations of mucus and secretions which lavage/cleaning solution alone may not. Thus, the turbulent airflow helps to provide improved cleaning of the distal end 208a of the catheter 208.

Figure 3D:
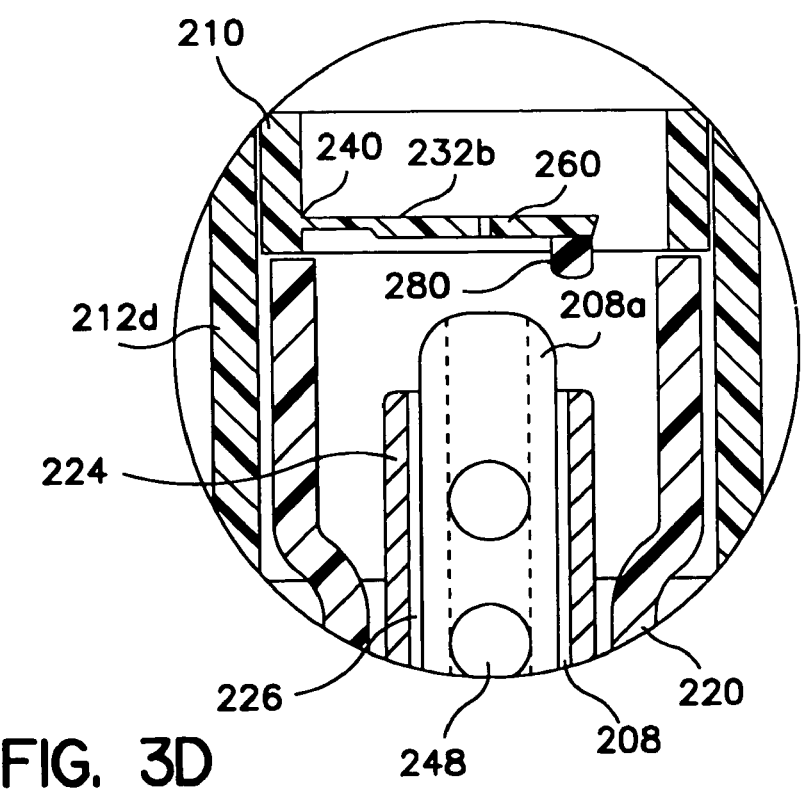
FIG. 3D shows a fragmented, close-up cross-sectional view of another embodiment of the improved respiratory suction catheter apparatus shown in FIG. 3A.

Turning now to FIG. 3D, there is shown yet another variation of the flap valve 232 shown in FIGS. 3A and 3B. Rather than having a channel formed in a proximal side thereof, the flap valve 232 has an aperture 260 formed therein so as to create an additional pathway for air to pass through the flap valve 232. As with the embodiment shown in FIG. 3A, the small aperture 260 creates more turbulent airflow at the distal end 208a of the catheter 208 and thereby improves cleaning. It is currently believed that an aperture 260 in the flap valve 232 with a diameter of about 0.76 mm (0.03 inches) is preferred.

Figure 4A:
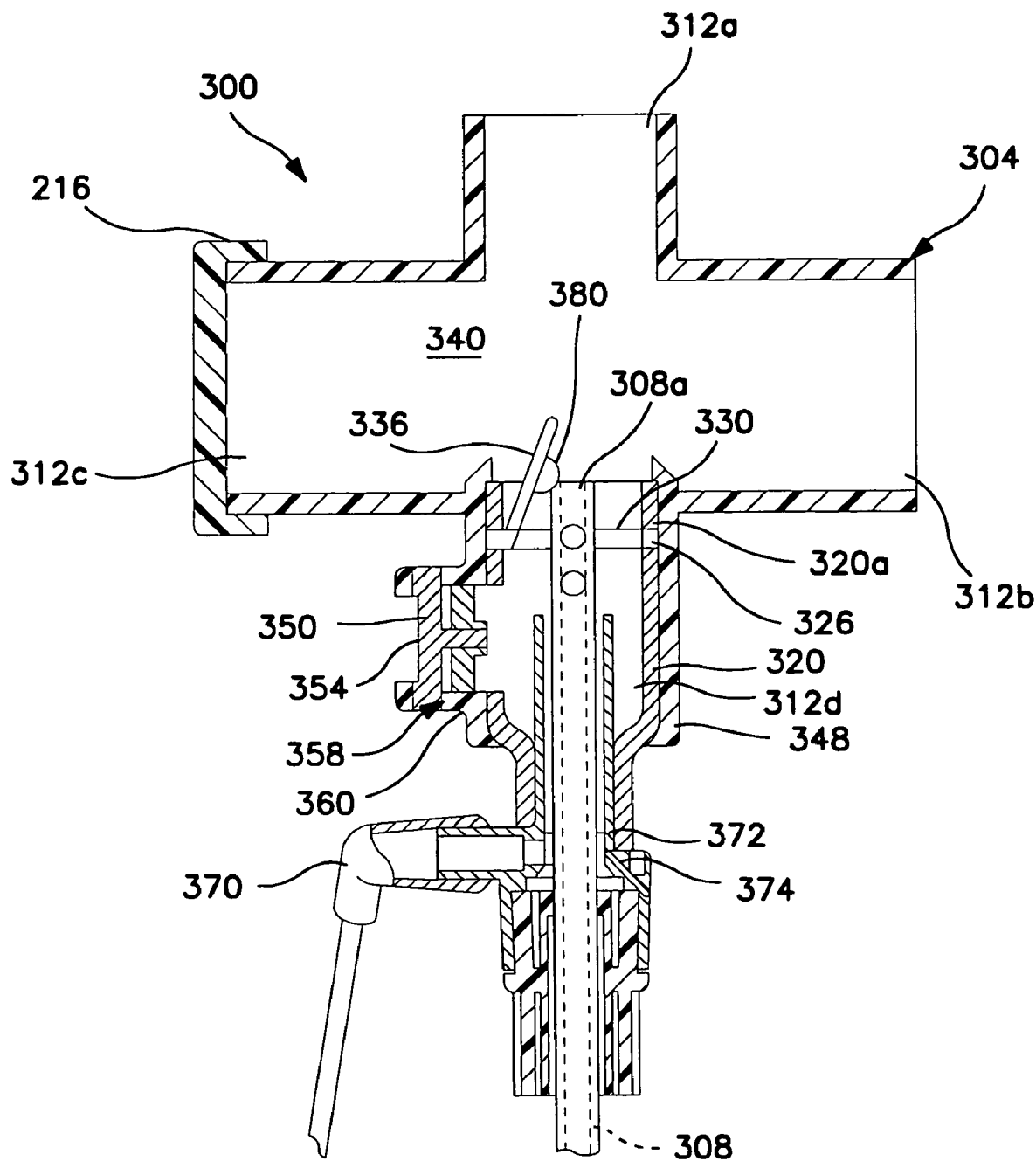
FIG. 4A shows a cross-sectional fragmented view of the manifold and catheter assembly wherein the catheter has translated through the assembly such that the improved flap has been uniformly deflected.

Turning now to FIG. 4A, there is shown another embodiment of an improved respiratory suction catheter apparatus, generally indicated at 300, with an improved flap 336 comprising at least one protrusion 380 made in accordance with the principles of the present invention. The improved respiratory suction catheter apparatus 300 includes a manifold 304 and a catheter 308. As with the previous embodiment, the manifold 304 includes a first port 312a, a second port 312b, an optional third port 312c, and an optional fourth port 312d.

An adapter 320 is disposed in the fourth port 312d in such a manner as to make the manifold 304 and the catheter 308 a functionally integrated unit. The adapter 320 may be adhesively attached to the manifold 304, or may be simply force-fit.

Unlike the embodiment discussed with FIGS. 3A–3D, an annular ring is not disposed in the manifold 304 independent of the adapter 320. Rather, an annular ring 326 extends inwardly from a distal end 320a of the adapter 320. The annular ring 326 defines an aperture or opening 330 through which the catheter 308 can be extended. Thus, the opening 330 is slightly larger than the exterior of the catheter 308.

Also extending inwardly from the adapter 320 is a flap 336. The flap 336 is preferably hingedly attached to either the adapter directly or to the annular ring 326. When no suction is applied to the catheter 308, or when the distal end 308a of the catheter is disposed distally from the flap 336, the flap 336 will generally extend distally from the annular ring 326 and provide virtually no resistance to advancement of the catheter 308. In this configuration, at least one protrusion 380 on the proximal side of flap 336 will interface with catheter 308 during this advancement such that the translation of catheter 308 through the assembly 300 will cause flap 336 to be deflected such that at least one protrusion 380 is the interfacing zone between catheter 308 and flap 336 during this period. In this configuration, the advancement of catheter 308 will cause a distal tip 308a of catheter 308 to encounter and displace flap 336 by contract with at least one protrusion 380. As shown in FIG. 4D, flap 336 comprising at least one protrusion 380 is deflected such that flap 336 remains in working condition and parallel to the advancement of catheter 308. The major benefit of each protrusion 380 is not realized until retraction of catheter 308, laden with secretions. This arrangement ensures that catheter 308 may be advanced with virtually no resistance and the planar surface of flap 336 will have less interaction with catheter 308 during retraction. When catheter 308 is retracted, mucus and similar secretions on catheter 308 will not be able to coat or collect on flap 336, especially the distal surface 336b of flap 336. Because at least one protrusion 380 formed or otherwise attached to flap 336 on its proximal surface 336a distances flap 336 from catheter 308 during this retraction, flap 336 is not positioned such that it will scrape this mucus and secretions from catheter 308 such that this mucus and secretions will not collect on the distal surface 336b of flap 336. During withdrawal, at least one protrusion 380 on the proximal side may actually remove some of the mucus and secretions coating catheter 308. The mucus and secretions will collect on each protrusion 380 on the proximal surface 336a of flap 336. These secretions can be easily removed during the cleaning of the catheter 336.

Figure 4B:
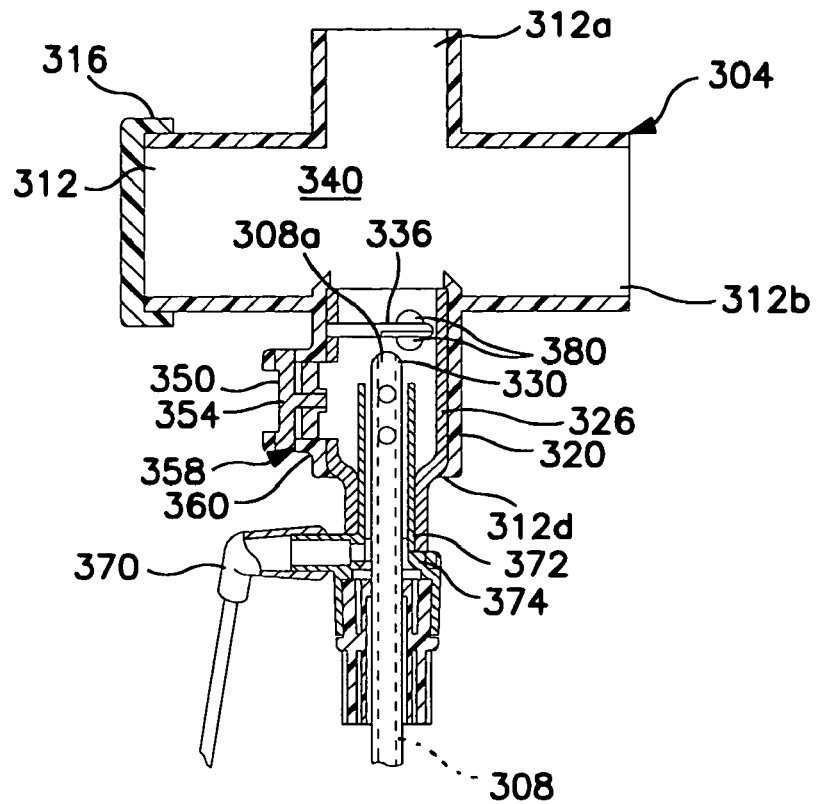
FIG. 4B shows a fragmented, cross-sectional view of the embodiment of FIG. 4A, wherein the improved valve is in a nearly closed position to isolate the catheter from the ventilation circuit.

As shown in FIG. 4B, as the distal end 308a of the catheter 308 is withdrawn through the annular ring 326 while suction is applied vacuum is created that pulls the flap 336 over the opening 330. The suction at the distal end 308a of the catheter 308 is reduced and more of the airflow in the ventilation circuit is available for the attached patient. While the flap 336 could be configured in the manner shown in FIGS. 3C and 3D, the present configuration does not necessitate the use of makeup air from the ventilation circuit 340.

If the catheter 308 were simply left in the chamber 348 behind the flap 336/annular ring 326 and lavage were injected into the chamber, it is possible that the cleaning process would be less efficient. Moreover, it may be difficult to suction mucus and other secretions from the chamber once the lavage source had been sucked dry. To overcome these problems with the prior art, the embodiment in FIGS. 4A through 4D comprises a makeup air inlet, generally indicated at 350, which is formed in a portion of the wall defining the fourth port 312d of the manifold and the adapter 320. The makeup air inlet 350 preferably includes a filter 354 that is selected to substantially prevent cross-contamination between the environment/clinicians and the patient. Disposed adjacent to the filter material is a flexible barrier 358 which forms a one-way valve 360.

Figure 4C:
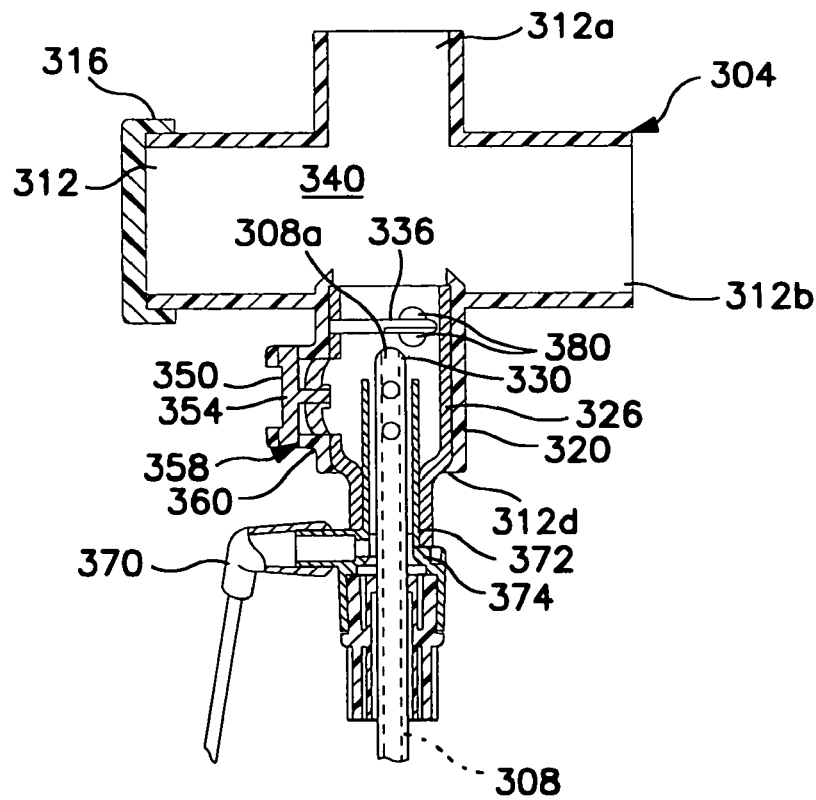
Figure 4D:
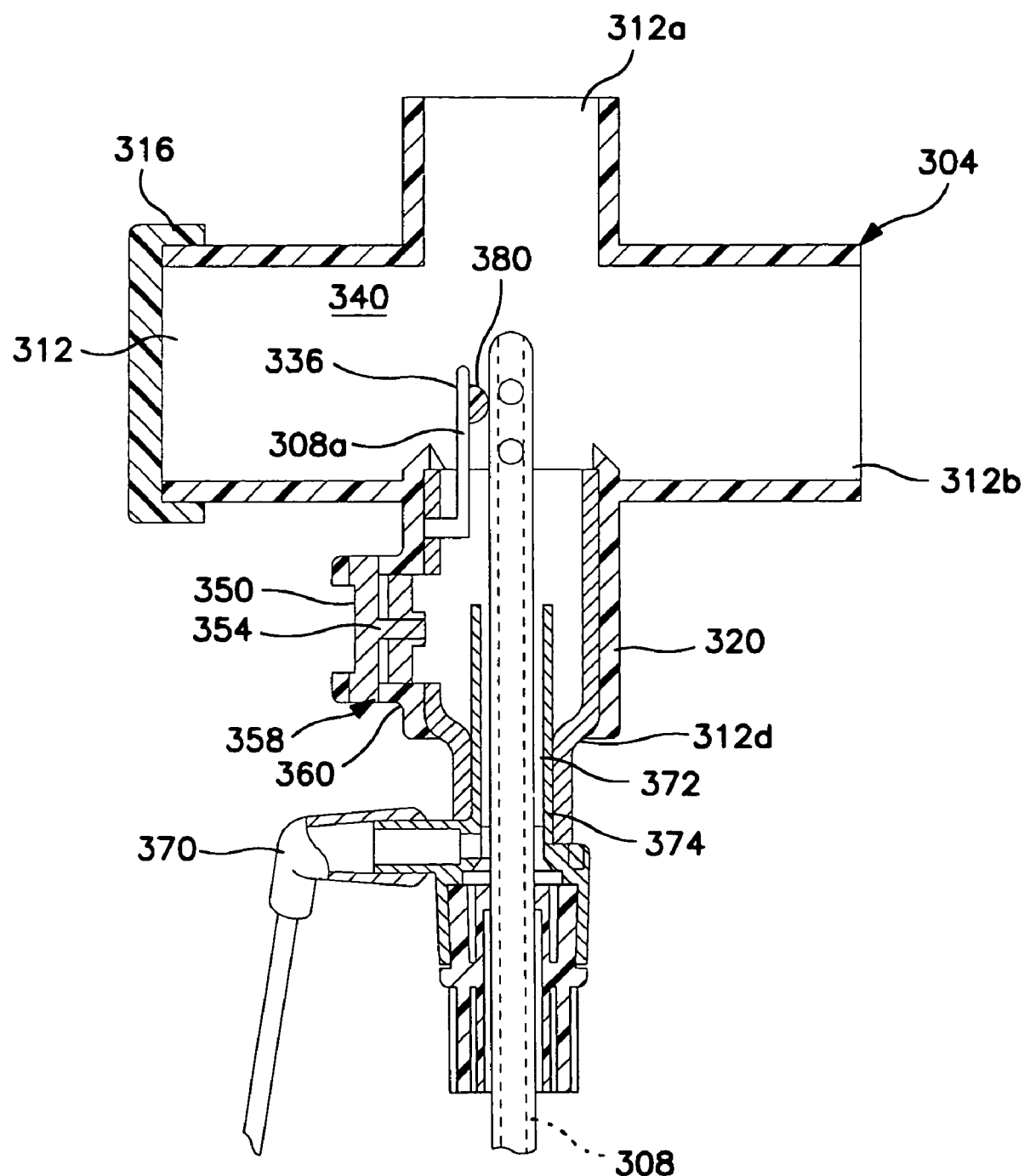
FIG. 4D shows a fragmented, cross-section view of the embodiment of FIGS. 4A–4C wherein the catheter has transferred throughout the assembly such that the improved valve has been uniformly deflected.

As shown in FIGS. 4B and 4C, the one-way valve 358 will generally be closed when the catheter 308 is in an extended position such that the catheter 308 extends through the opening 330 in the annular ring 326. However, once the distal end 308a of the catheter 308 has been withdrawn through the opening 330 in the annular ring 326 and the flap 336 has been drawn closed, a vacuum may develop on the side of the flap 336 opposite the ventilation circuit 340. The vacuum causes the one-way valve 358 to open and allow a supply of makeup air to enter the chamber. The makeup air flowing past the flexible one-way valve member 358 helps to create turbulent airflow and facilitate removal of any respiratory secretions on the catheter 308. This is preferably accomplished at about the same time the user utilizes the lavage port 370 to inject lavage/cleaning solution through the space 372 between the collar 374 and the catheter 308. It will be appreciated that the one-way valve 358 could be configured to provide very little resistance to air inflow, or could be configured to require a substantial vacuum to be present before makeup air is allowed into the area proximal the flap 336.

Figure 5A:
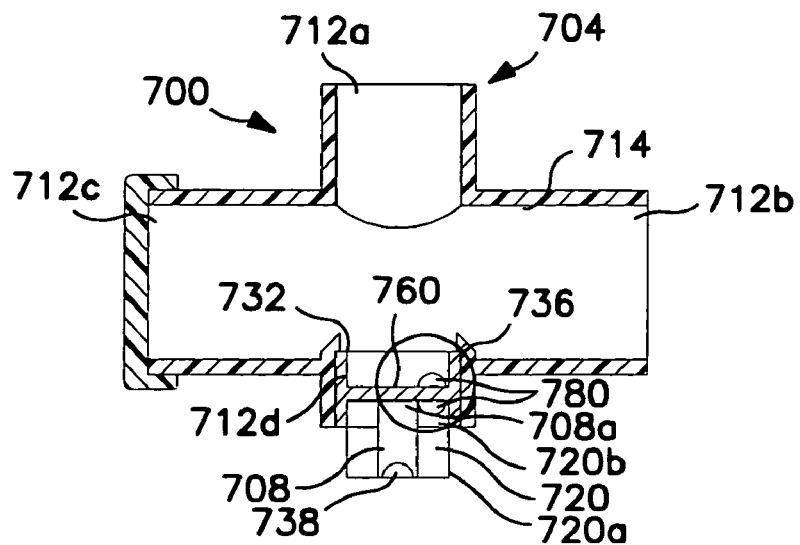
FIG. 5A shows a fragmented, cross-sectional view of an improved endotracheal catheter wherein the valve mechanism locks in a nearly closed position.

Turning now to FIG. 5A, there is shown a fragmented, cross-sectional view of an alternate embodiment of an improved endotracheal catheter system, generally indicated at 700, incorporating aspects of the present invention. The endotracheal catheter system includes a manifold, generally indicated at 704, and a catheter 708. As with several of the previous embodiments, the manifold 704 may include a plurality of ports 712a–712d. The first port 712a is configured for attachment to the proximal end of an artificial airway, such as the hub of an endotracheal tube, tracheostomy tube, or similar airway. A second port 712b is typically connected to a pair of ventilator tubes (not shown) by means of an adapter (not shown), in accordance with common practice in the art. During normal usage, conditioned inspiratory air is forced through one of the ventilator tubes, through the second port 712b and the first port 712a and into the patient's lungs via the artificial airway. Exhaled air is carried through the first port 712a and then the second port 712b and out through the other ventilator tube. Thus, the manifold 704 forms part of a ventilation circuit 714 through which respiratory air is cycled.

Also forming part of the manifold 704 is a third port 712c. The third port 712c is typically covered by a cap 716 that may be removed to facilitate "blow-by" and thereby enable the patient to gradually resume spontaneous breathing. Those skilled in the art will appreciate that while the provision of a third port for blow-by is preferred, it is not necessary to the practice of the principles of the invention.

The manifold 704 also has a fourth port 712d. The fourth port 712d is disposed generally opposite the first port 712a and is configured to allow the catheter 708 to slide therethrough and into the first port to enable suctioning of the patient. At the completion of suctioning, the catheter 708 is pulled back into the fourth port 712d to facilitate cleaning and to prevent interference with the ventilation circuit 714.

Disposed between the wall forming the fourth port 712d and the catheter 708 is a coupling or adapter 720. On an outer extreme, the adapter 720 engages the wall defining the fourth port 712d. On an inner extreme, the adapter 720 engages the catheter 708. Alternatively, a collar such as collar 224 shown in FIG. 3A could be used between the catheter 708 and the adapter 720.

The adapter 720 preferably has a cylindrical hollow which forms a first portion 720a disposed toward a proximal end thereof, and a second portion 720b disposed toward a distal end thereof. At the first portion 720a, the diameter of the cylindrical hollow is substantially the same as the outer diameter of the catheter 708 so that the first portion 720a of the adapter 720 closely surrounds the catheter.

The second portion 720b of cylindrical hollow of adapter 720 has a larger diameter than the first portion 720a of adapter 720. This larger diameter forms a collection area in which mucus and other secretions can collect as the catheter 708 is drawn proximally through the adapter 720.

As has been mentioned previously, in accordance with one of the principles of the present invention it has been found that selective obstruction of the airflow into the distal end 708a of the catheter 708 can significantly improve catheter cleaning. Additionally, it has been found that such a mechanism for improved cleaning also minimizes the withdrawal or air from the ventilation circuit 714.

As shown in FIG. 5A, a flap 732 is hingedly attached to an annular ring 736 disposed inside the fourth port 712d so as to enable the flap 732 to pivot with respect to the ring. Alternatively, flap 732 could be attached directly to the wall of the manifold 704 defining the fourth port 712d or to the adapter 720. The hinged attachment 740 allows the flap 732 to selectively move while maintaining alignment with the distal end 708a of the catheter 708, thereby creating a flap valve. As shown, flap 732 comprises at least one protrusion 780 on the proximal surface of flap 732 that may interface or otherwise engage catheter 708 at distal tip 708a. Flap 732 may comprise an aperture 760 formed in flap 732 to provide a conduit for a controlled amount of air to enter catheter 708 at distal end 708a. As with previous embodiments, the aperture 760 also allows a small amount of air to enter the catheter 708 and further facilitate cleaning without drawing excessive air from the inhalation circuit of the patient.

With the flap 732 significantly reducing of the airflow into the distal end 708a of the catheter 708, suction will increase at the lateral openings 738, partially shown in FIG. 5A, which are formed in the catheter proximal from the distal end 708a and ultimately improve the cleaning of the catheter 708.

One significant difference between the flap 732 and those shown in previous embodiments is the manner in which it engages the ring 736. On one end, the flap 732 is pivotally attached to the ring 736 to enable movement as a flap valve as discussed above. At an opposing end, the flap 732 is configured to engage a flange 764 that extends inwardly from the ring 736. More specifically, the ends of the flap 732 and the flange 764 are configured to complement one another so as to nest in one another or otherwise form a locking engagement. Thus, as shown more clearly in FIG. 5B, the end 764a of the flange 764 is provided with a V-shaped groove and the complimentary end 732a of the flap 732 is V-shaped projection.

As the catheter 708 is withdrawn through the adapter 720 to the point where the distal end 708a of the catheter is disposed behind the ring 736, the suction of air through the tube will cause the flap 732 to be pulled toward the distal end 708a of the catheter 708 and thereby improve cleaning of the catheter as has been discussed with previous embodiments. As previously discussed, at least one protrusion 780 on the proximal surface 732a of flap 732 will significantly reduce the interaction between catheter 708 and flap 732 during retraction and prevent the accumulation of mucus and similar secretions on the distal surface 732b of flap 732.

Once the catheter 708 is sufficiently-withdrawn through the adapter 720, the end 732c of the flap 732 will nest in the groove in the end 764a of the flange 764, thereby locking the flap 732 in a closed position. With the flap 732 locked closed, the risk of mucus or other secretions seeping into the ventilation circuit 714 is significantly reduced.

Thus, the engagement between the flap 732 and the flange 764 provides a locking mechanism which prevents flap 732 from being moved from the nearly closed position (FIG. 5B) to the open position wherein the flap 732 does not interfere with distal movement of the catheter 708. As shown in prior embodiments, suction maintained the flap 732 in the closed position. In contrast, the present embodiment provides a positive retention of flap 732.

When suctioning is desired, flap 732 may be opened by advancing the distal end 708a of the catheter 708 to contact at least one protrusion 780 on flap 732 and force the end 732a of flap 732 out of engagement with the flange 764. The amount of force required is minimal above that normally exerted to advance the catheter 708 for suctioning.

Figure 5B:
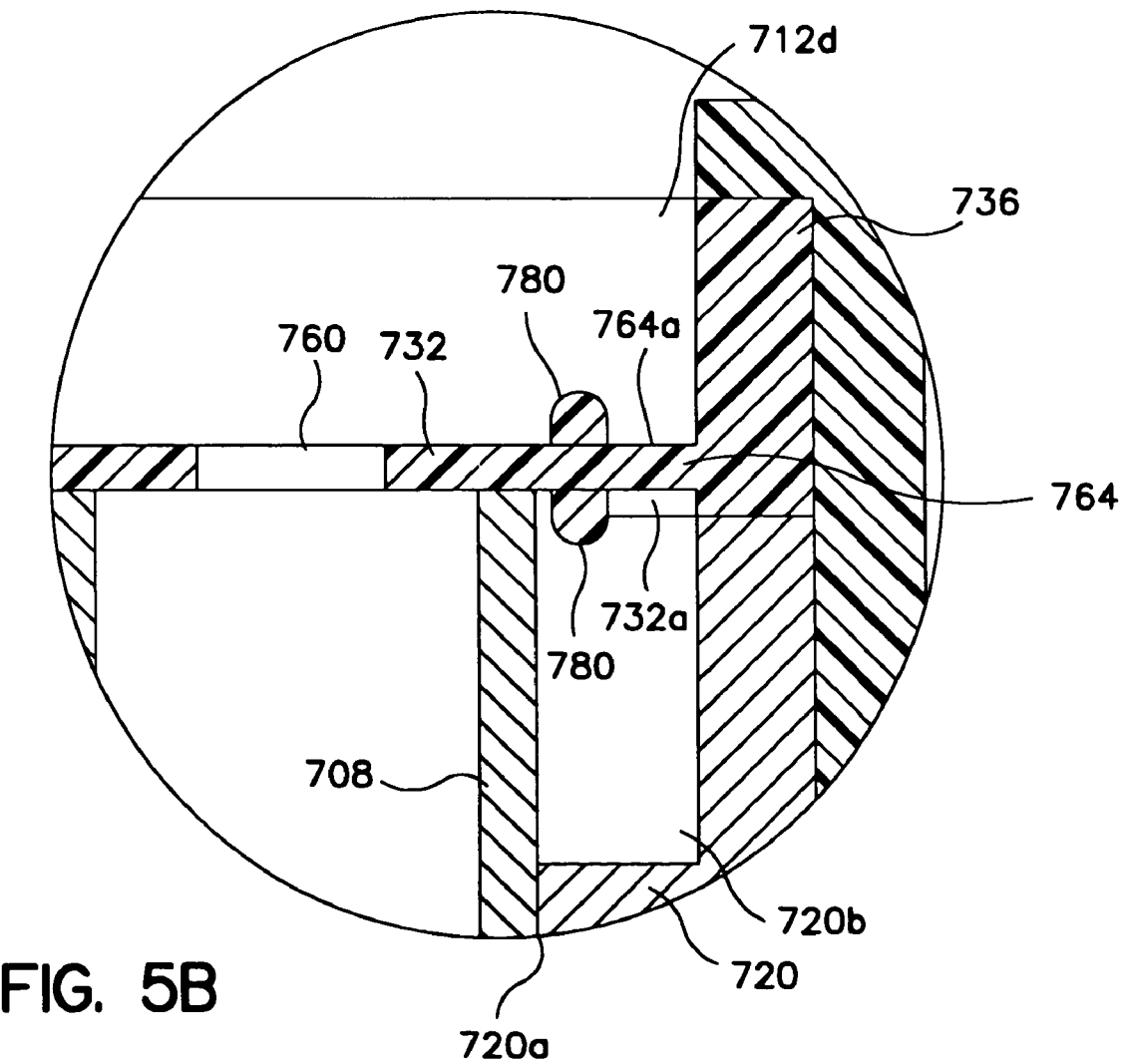
FIG. 5B shows a close-up view of the locking valve mechanism and associated structure of FIG. 5A.

While not shown in FIGS. 5A and 5B, a lavage port could be used with the adapter 720 to enhance cleaning of the catheter 708. The lavage port could be placed along the first or second portions, 720a or 720b, depending on the tolerances thereof.

Figure 6A:
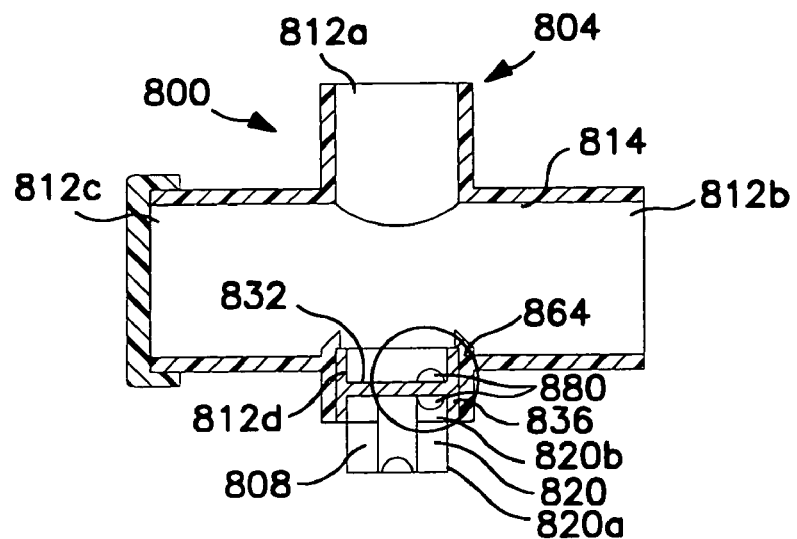
FIG. 6A shows a fragmented, cross-sectional view of an alternate embodiment of an improved endotracheal catheter with a locking valve mechanism.

Turning now to FIG. 6A, there is shown a fragmented, cross-sectional view of an alternate embodiment of an improved endotracheal catheter system, generally indicated at 800. As with the previous embodiment, the endotracheal catheter system includes a locking valve mechanism, generally indicated at 810.

The endotracheal catheter 800 includes a manifold, generally indicated at 804 and the catheter 808. The manifold includes first, second, third and fourth ports, 812a–812d which define a ventilation circuit 814 and otherwise function in the same manner as the first through fourth ports 712a–712d discussed above in FIG. 5A.

An adapter 820 is disposed in the fourth port 812d in a manner similar to that discussed with respect to the prior embodiment. The adapter 820 may include first and second portions 820a and 820b having different diameters to facilitate collection of mucus and other secretions, and to otherwise improve the workings of the device.

Also disposed in the fourth port 812d is a flap 832 that is configured to approach the distal end 808a of the catheter 808. As with the previous embodiments, at least one protrusion 880 is preformed on at least the proximal surface of flap 832 to prevent the direct communication between catheter 808 and flap 832. This arrangement not only protects flap 832 from being deformed during the translation of catheter 808 by focusing the pressures of the advancement of catheter 808 onto protrusion 880 but also improves the cleaning of catheter 808 by preventing the planar surface of flap 832 from scraping the mucus and secretions onto the distal surface of flap 832. Flap 832 is pivotally attached to a ring 836 disposed in the fourth port 812d. Alternatively, the flap 832 could be directly connected to the wall defining the fourth port 812d. As with several of the previously discussed embodiments, the flap 832 is drawn into contact with the distal end 808a of the catheter 808 via at least one protrusion 880 as suction is applied through the catheter 808. Preferably, forming at least one aperture 860 in flap 832 provides an additional conduit for airflow. This reduced airflow improves cleaning. The size of the aperture 860 is preferably about 0.76 mm (0.03 inches) in diameter.

Also disposed on the ring 836 is an inwardly extending projection 864 that forms a catch. Preferably, the projection 864 is disposed on the ring 836 opposite the location at which the flap 832 is attached to the ring. As with the flap 832, the projection may be directly mounted on in the fourth port 812d.

As the flap 832 is drawn proximally by suction through the catheter 808, the flap passes over the projection 864 which extends inwardly slightly further than the end 832a of the flap. Thus, once the flap 832 has moved proximally beyond the extreme inward point of the projection 864, distal movement of the flap is restricted by the projection. Thus, the flap 832 becomes frictionally engaged behind the projection 864 until is forced distally past the projection by advancement of the catheter 808. Alternatively, those skilled in the art will appreciate that the flap 832 could be configured to bias the flap 832 into the proximal or closed position.

Figure 6B:
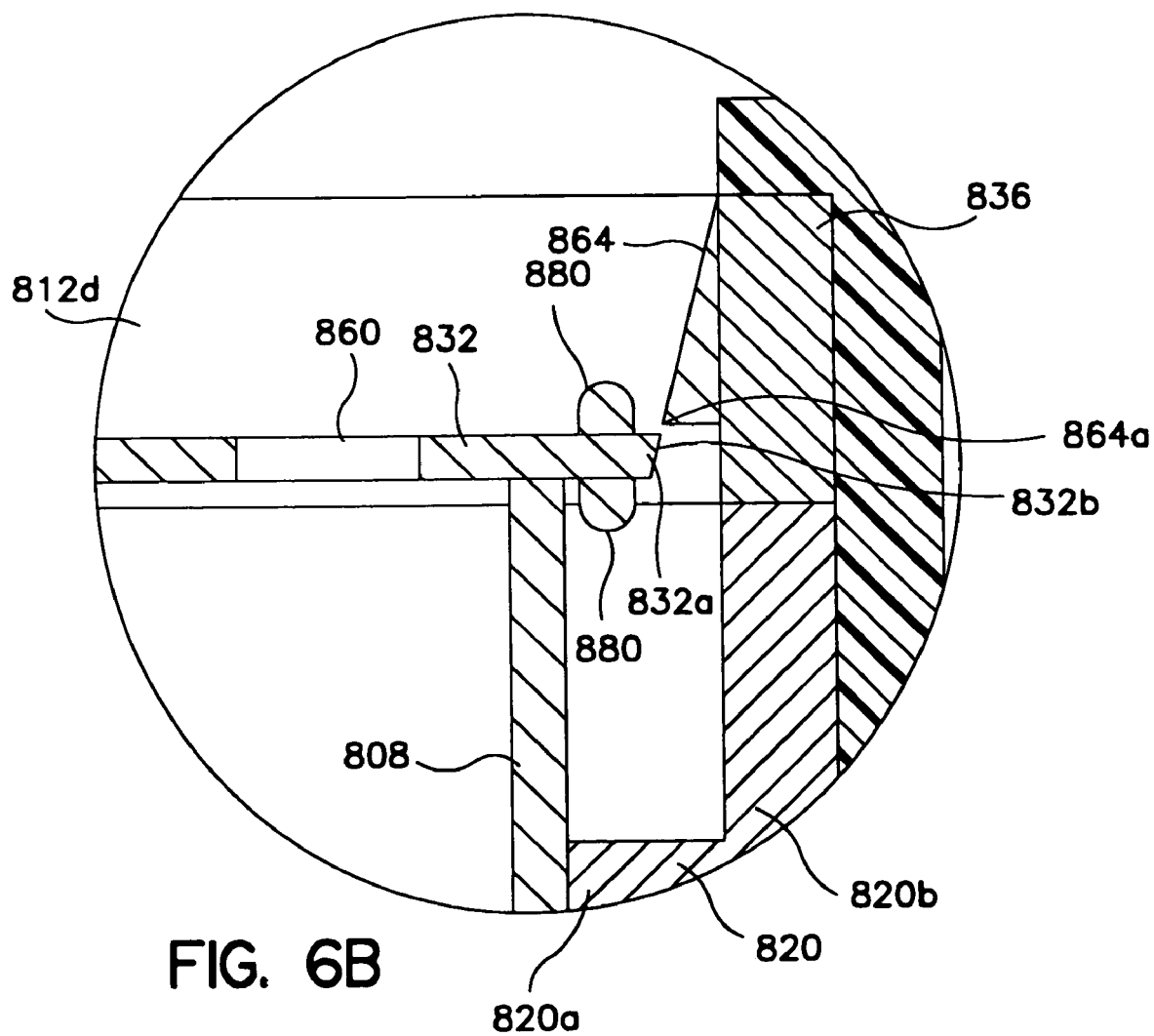
FIG. 6B shows a close-up view of the locking valve mechanism and associated structure of FIG. 6A.

Referring specifically to FIG. 6B, there is shown a close-up view of the locking valve mechanism and locking structure discussed above. As shown, the end 832a of the flap 832 is tapered to a point 832b that is formed on the distal side of the flap 832. The projection 864 tapers toward a point disposed at the proximal end 864a thereof. Such a configuration enables the end 832a of the flap 832 to slide proximally over the projection 864, while requiring additional effort to move the flap distally past the projection 864.

Figure 7A:
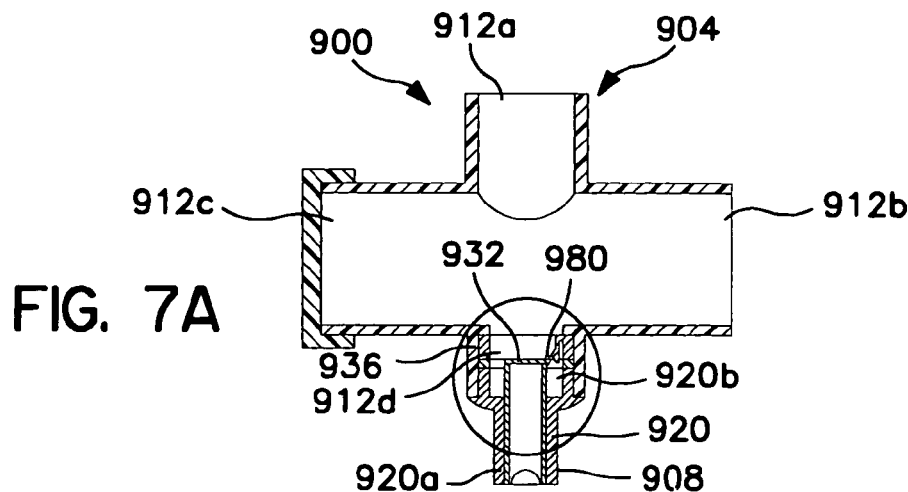
FIG. 7A shows a fragmented, cross-sectional view of another embodiment of an improved endotracheal catheter that has a locking valve mechanism disposed thereon.

FIG. 7A shows a cross-sectional view of yet another embodiment of an improved endotracheal catheter generally indicated at 900. The catheter 900 includes a manifold 904 and a catheter 908. The manifold 904 includes first, second, third and fourth ports, 912a–912d, the first and fourth of which are aligned to allow advancement of the catheter 908 through the manifold.

An adapter 920 is disposed in the fourth port 912d and functions as a guide for the catheter 908 as it is advanced and retracted. The adapter 920 preferably includes a first portion 920a having a inner diameter approximately the same size as the outside diameter of the catheter 908, and a second portion 920b having a diameter which is larger than that of the first portion.

Also disposed in the fourth port 912d is a pair of rings 936a and 936b. A flap 932 is attached to the ring 936b and extends inwardly so as to be disposed perpendicular to the travel path of the catheter 908 as it is advanced through the manifold 904. The flap 932 preferably has a small hole 960 to allow a small amount of air through the flap 932. As with the previous embodiments, flap 932 may further comprise at least one protrusion 980 on at least the proximal surface of flap 932. In this configuration, protrusion 980 prevents catheter 908 from sliding on the planar surface of flap 932 during translation. During the arrangement shown in FIGS. 7A–7B, suction is reduced at aperture 944 in the distal tip 908a of catheter 908. This reduces suction at aperture 944 and increase suction at aperture 948 shown in FIG. 7A for cleaning catheter 908 and a portion of manifold 904.

Figure 7B:
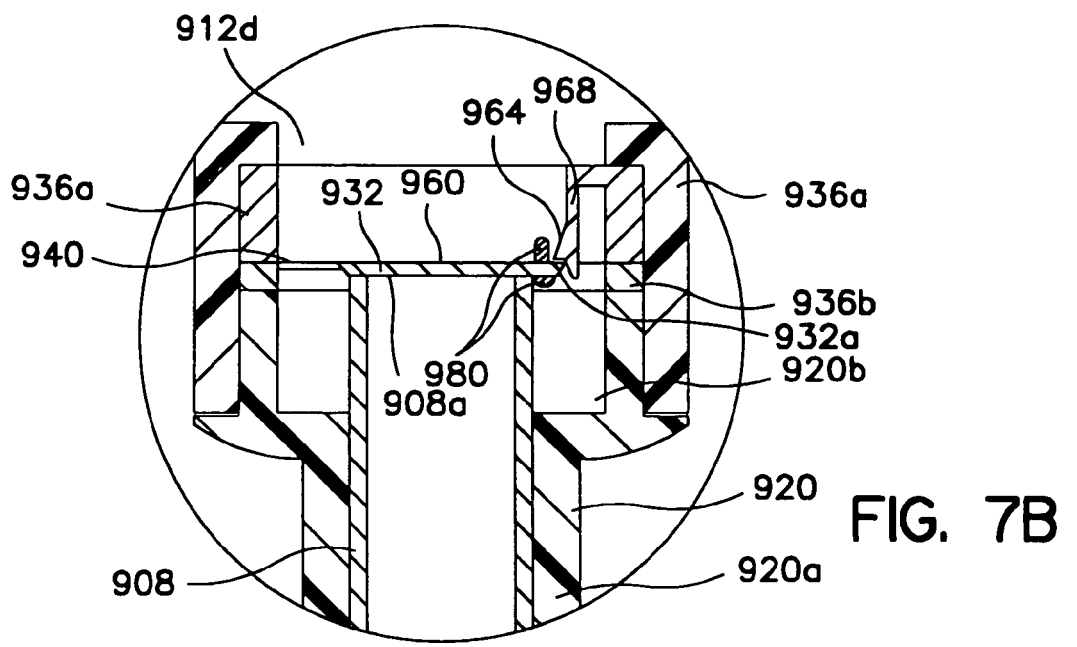
FIG. 7B shows a close-up view of the locking valve mechanism and associated structure of FIG. 7A.

Referring more specifically to FIG. 7B, the flap 932 is pivotally attached to the ring 936b so that as the distal end 908a of the catheter 908 is withdrawn through the fourth port 912d, suction from the catheter draws the flap 932 into contact with the distal end 908a. In such a manner, the flap 932 functions as a flap valve to substantially occlude the distal end 908a of the catheter 908.

Also shown more clearly in FIG. 7B a catch 964 is attached by an arm 968 to the ring 936a. The catch 964 is configured to engage the flap 932 to lock the flap in a desired location. As the catheter 908 is withdrawn through the fourth port 912b, the flap 932 is drawn by the suction effect at the distal end 908a. The end 932a of the flap 932 opposite the attachment arm 940 between the flap 932 and the ring 936b engages the catch 964 and causes the catch to be deflected out of the way. Once the end 932a of the flap 932 has passed by the catch 964, the catch moves back into its normal position. In such a position, the catch 964 engages the end 932a of the flap 932 and locks the flap 932 in a proximal, closed position. To release the flap 932, the catheter 908 is advanced with sufficient force to cause the catch 964 to deflect out of the way. The flap 932 may then pivot distally and the catheter 908 advanced.

Figure 7C:
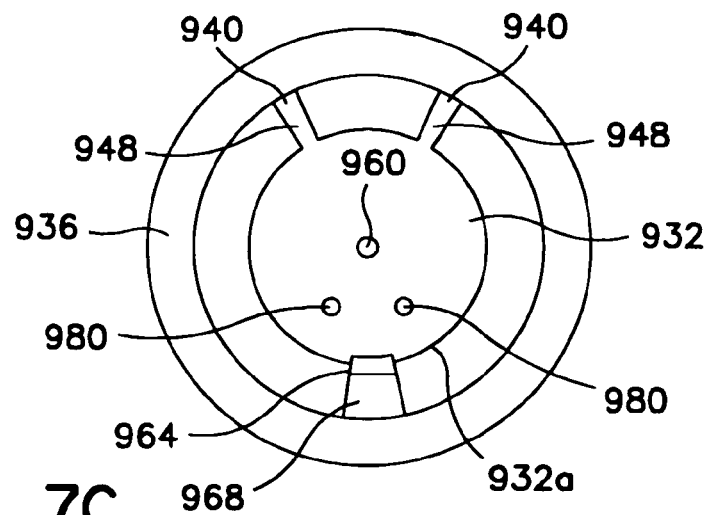
FIG. 7C shows a close-up end view of the locking valve mechanism of FIGS. 7A and 7B.

Turning now to FIG. 7C, there is shown an end view of the flap 932, the rings (shown jointly as 936) and associated structure. The flap 932 is attached to the ring 936 by two arms 948, each forming an attachment point 940. The opposite end 932a of the flap 932 engages the catch 964 that is attached to the ring 936 by an arm 968. The catch 940 effectively locks the flap 932 in a proximal position until the user forcibly advances the catheter in a distal direction, causing the catch to release the flap. As shown, a plurality of protrusions 980 is formed on at least one surface of flap 932.

Those skilled in the art will appreciate that numerous modifications could be used to accomplish the principles of the present invention. As an example, a single arm 948 could be used with the flap 932, and multiple catches 964 could be used. Likewise, a single ring could be used rather than the first and second rings 936a and 936b to support the flap 932 and the catch 968. Furthermore, as is shown in FIG. 7D, modifications can be made the flap 932a to provide other benefits.

Figure 7D:
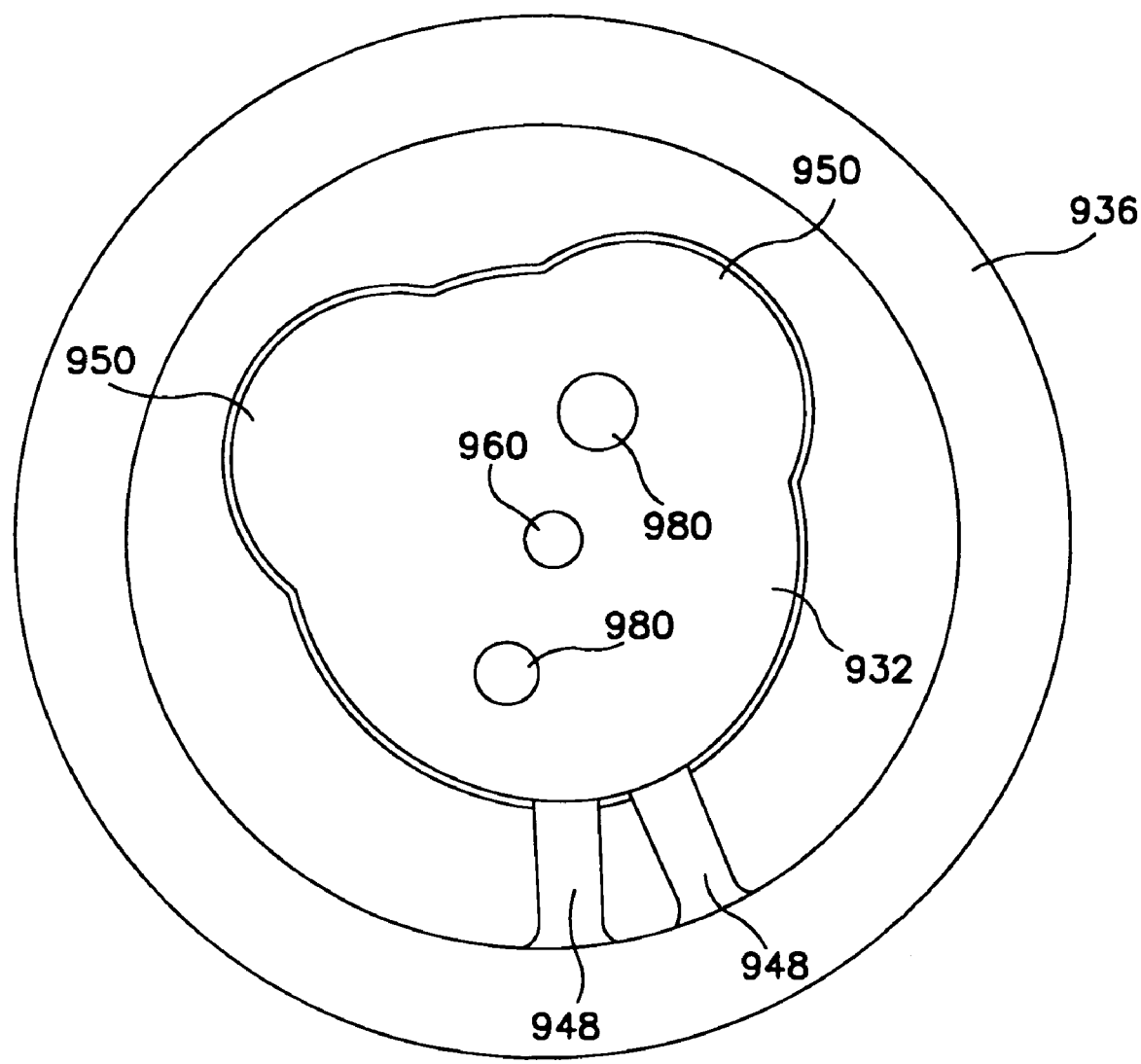
FIG. 7D shows a close-up end view of an alternate embodiment of the flap valve shown in FIG. 7C.

As shown in FIG. 7D, a pair of arms 948 attaches the flap 932 to the ring 936. As mentioned above, the arms 948 could be configured to bias the flap 932 into the closed position. The flap 932 is generally circular, but has two rounded projections 950 which extend outwardly and are spaced approximately 90 degrees apart. The projections serve two important purposes. First, even if the generally circular portion of the flap 932 were slightly smaller than the distal opening of the endotracheal tube, the projections 950 would prevent the flap from entering the endotracheal tube. Second, the projections 950 would cause the flap to align for airflow to continue to the patient without lying flat to cover any passage which might interfere with airflow to or from the patient.

Also shown in FIG. 7D is the aperture 960 that is formed in the generally circular portion of the flap 932a. As shown the aperture 960 is between about 0.76 mm (0.03 inches) and about 1.02 mm (0.04 inches) in diameter. While shown as being circular or disk-shaped, those skilled in the art will appreciate, in light of the present disclosure, that other shaped apertures could also be used. As shown, a plurality of protrusions 980 are be formed on at least the proximal surface of flap 932.

Figure 8A:
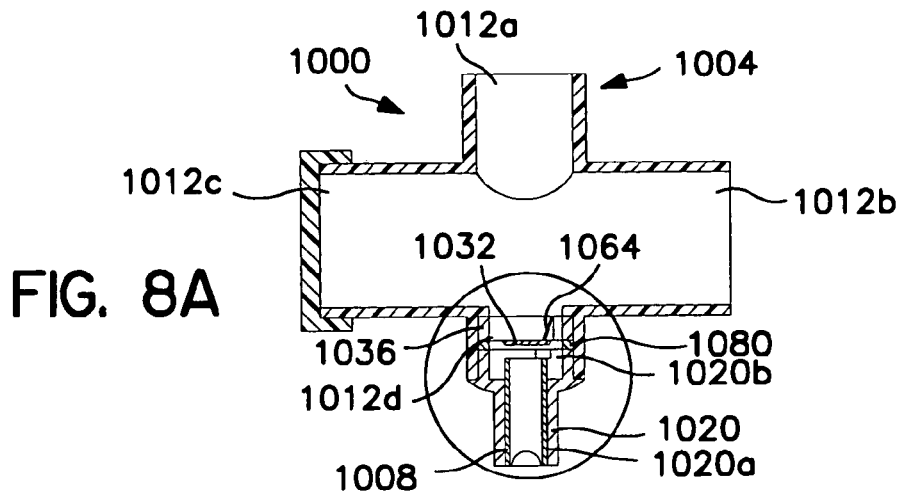
FIG. 8A shows a fragmented, cross-sectional view of yet another embodiment of an improved endotracheal catheter that has a locking mechanism disposed thereon.

Turning now to FIG. 8A, there is shown a side cross-sectional view of an improved endotracheal catheter, generally indicated at 1000. The improved endotracheal catheter 1000 includes a manifold, generally indicated at 1004, and a catheter 1008. The manifold 1004 includes first, second, third and fourth ports 1012a–1012d as set forth above.

An adapter 1020 is disposed in the fourth port 1012d and facilitates advancement and withdrawal of the catheter 1008 through the manifold 1004. While shown as having a first portion 1020a with a smaller diameter and a second portion 1020b with a larger diameter, the adapter 1020 could be made with a uniform interior diameter. In the alternative, the wall defining the fourth port 1012d could be configured to eliminate the need for an adapter 1020.

Also disposed in the fourth port 1012d is a flap 1032 that is connected to a ring 1036. The flap 1032 extends inwardly from the ring 1036 and is configured to be disposed perpendicular to the long axis of the catheter 1008. As shown, flap 1032 further comprises at least one protrusion 1080 formed on at least the proximal surface of flap 1032. In this configuration, protrusion 1080 interfaces with catheter 1008 such that the planar surface of flap 1032 cannot scrape the mucus and other secretions coating catheter 1008 during retraction.

Figure 8B:
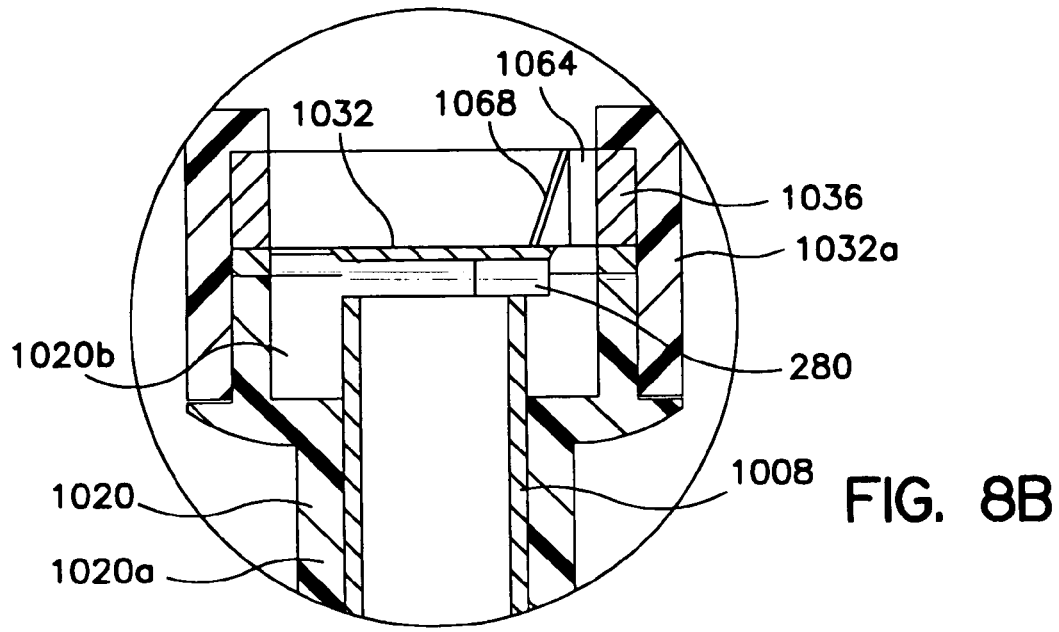
FIG. 8B shows a close-up view of the locking valve mechanism and associated structure of FIG. 8A.

Like the previous embodiment, the end 1032a of the flap 1032 engages a catch mechanism 1064 which extends inwardly. As shown more clearly in FIG. 8B, the catch mechanism 1064 is formed by at least one projection 1068 which extends proximally and inwardly from the ring 1036. As the flap 1032 is drawn proximally by the catheter 1008, the end 1032a of the flap is drawn over the projection 1068 that temporarily deflects. Once the flap 1032 has moved a sufficient distance proximally, the projection 1068 returns to its normal position and thereby locks the flap in the proximal position.

Figure 8C:
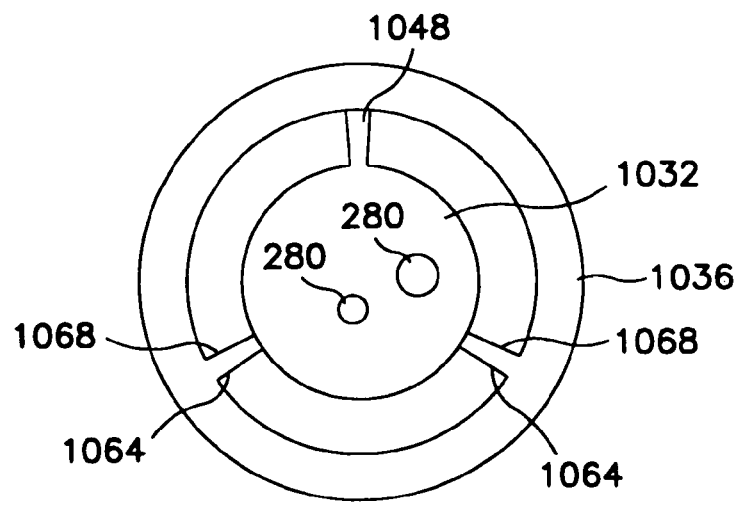
FIG. 8C shows a close-up end view of the locking valve mechanism of FIGS. 8A and 8B.

FIG. 8C shows an end view of the ring 1036 and the flap 1032. The flap 1032 is attached to the ring 1036 by a single arm 1048. A pair of catch mechanisms 1064 in the form of projections 1068 are spaced apart at 120 degree intervals. Having the catch mechanisms 1064 spaced helps to stabilize the flap 1032 when in the locked position. As shown, at least one protrusion 1080 may be formed on at least the proximal surface of flap 1032.

Figure 9A:
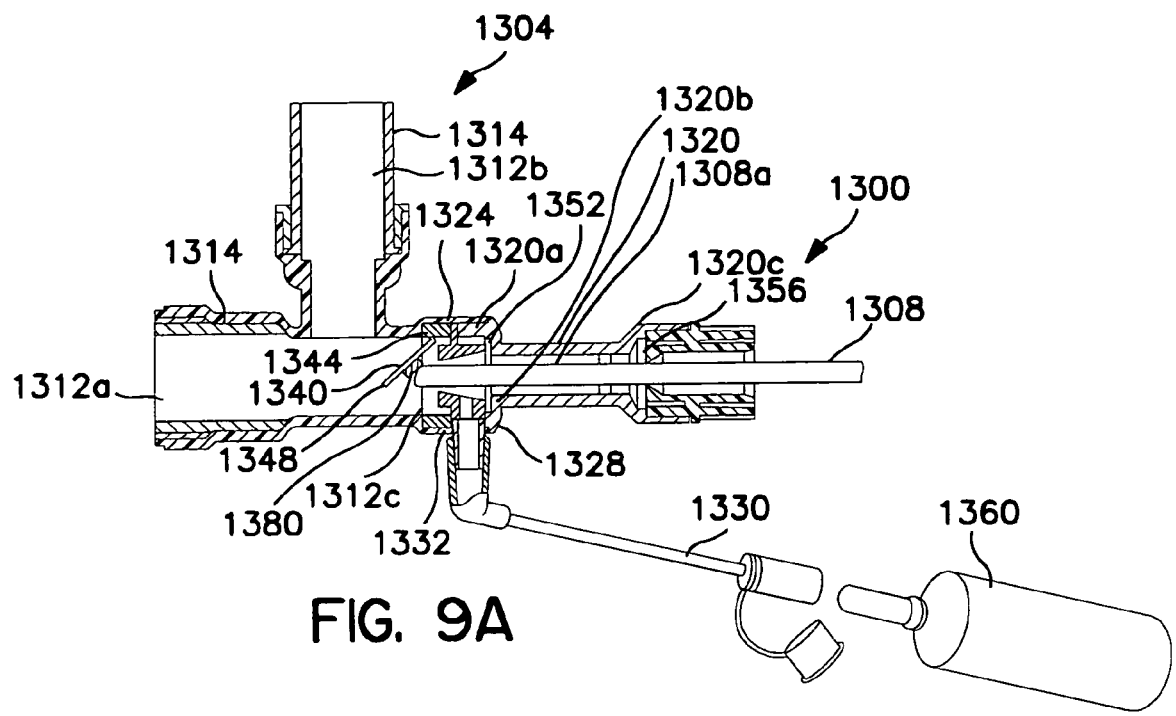
FIG. 9A shows a fragmented, cross-sectional view of an alternate embodiment of an improved endotracheal catheter in which a pair of wiper seals are used to enhance cleaning of the distal end of the catheter tube.

FIG. 9A shows a cross-sectional view of yet another embodiment of an endotracheal catheter system 1300 that incorporates aspects of the present invention. The endotracheal catheter system 1300 includes a manifold, generally indicated at 1304 which forms a fitting for connecting the endotracheal catheter 1300 to the artificial airway (i.e. endotracheal tube) of a patient. The endotracheal catheter system 1300 also includes an elongate catheter 1308.

The manifold 1304 includes a first port 1312a, a second port 1312b, and a third port 1312c. The first port 1312a is configured to engage an artificial airway, such as an endotracheal tube. The second port 1312b provides inspiratory and expiratory airflow to and from the patient. Typically, a Y-shaped adapter is attached to the second port 1312b. However, many configurations are used in the clinical setting and those skilled in the art will appreciate the different combinations that are available.

The third port 1312c is disposed opposite the first port 1312a. It is aligned such that the catheter 1308 can pass through the third port 1312c, through the manifold 1304, and through the first port 1312a into the artificial airway. As shown in FIG. 9A, the first and second ports 1312a and 1312b may also have swivel structures 1314 to enable the manifold 1304 to swivel with respect to adjoining structures and thereby improve patient comfort and flexibility.

Connected to the third port 1312c is a coupling or adapter 1320. On the outer surface of the distal end 1320a, the adapter 1320 engages the wall defining the third port 1312c. The inner surface of the adapter 1320 forms a chamber about the distal end 1308a of the catheter 1308. This chamber assists in cleaning the distal end of the catheter in a manner that will be discussed more fully below.

Disposed adjacent to the distal end 1320a of the adapter 1320 is a collar 1324 which has a frustoconical bore 1328 extending therethrough. Those skilled in the art will appreciate that the collar 1324 could be formed integrally with the adapter 1320 if desired.

When lavage solution is injected through a lavage port 1330 and a side opening 1332 into the frustoconical bore 1328, the collar 1324 helps to channel the lavage solution along the catheter 1308, through the first port 1312a and into the artificial airway.

The distal end 1324a of frustoconical bore forms an orifice in the distal end of the collar 1324. A flap 1340, supported by a support ring 1344 disposed in the third port 1312c selectively engages the orifice to substantially occlude the orifice when the two are engaged. As with prior embodiments, the flap 1340 preferably has one or more holes 1348 formed therein to allow a small amount of air through the flap. Also, like prior embodiments, the flap 1340 may be biased in the occluding position, or may be drawn into the occluding position by suction through the catheter 1308. Importantly, flap 1340 comprises at least one protrusion 1380 on the proximal surface of flap 1340 for the reason disclosed herein.

Disposed at the opposing, proximal end of the collar 1324 is a first wiper seal 1352. Preferably, a narrowed portion 1320b of the adapter 1320 supports the wiper seal 1352. Those skilled in the art, however, will appreciate that other mechanism for holding the wiper seal 1352 could be used. As the catheter 1308 is withdrawn past the first wiper seal 1352, the wiper seal removes major secretions. While discussed herein as a wiper seal, some other structure having close tolerances (i.e. one that would remove most secretions) could also be used.

From the wiper seal 1352, the adapter 1320 extends proximally and forms a cleaning chamber. Disposed adjacent a proximal end 1320c of the adapter 1320 is a second wiper seal 1356. As with the first wiper seal 1352, the object of the second wiper seal 1356 is to remove secretions from the exterior of the catheter 1308 as it is withdrawn from the artificial airway of the patient. However, the second wiper seal 1356 will typically have a smaller diameter opening so that the second wiper seal more closely engages the exterior of the catheter 1308 than the first wiper seal 1352.

Conventionally, a single wiper seal has been used. The wiper seal was placed in the location of the second wiper seal 1356 to wipe secretions from the catheter as it was withdrawn. The distal end 1308a of catheter 1308, however, was never physically wiped. Instead, the operator attempted to clean this portion with solution injected through a lavage port.

Figure 9B:
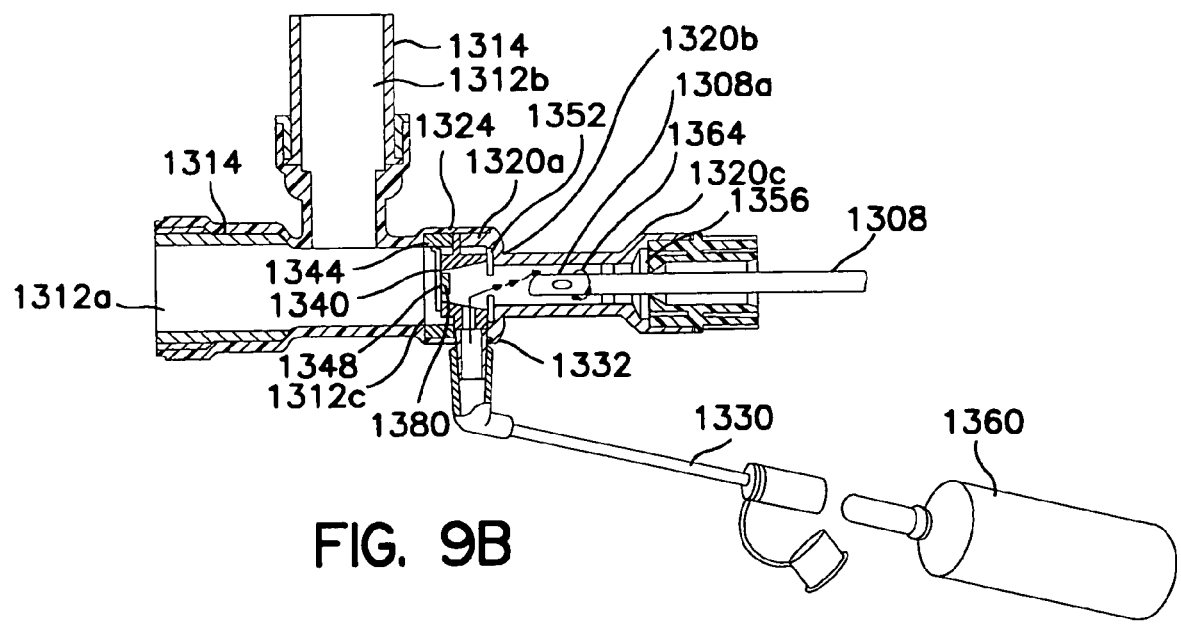
FIG. 9B shows a cross-sectional view similar to that of FIG. 10A, but with the catheter tube pulled back into a proximal position.

Turning now to FIG. 9B, there is shown a side cross-sectional view of the endotracheal catheter 1300 in which the catheter 1308 has been withdrawn through the manifold 1304 into a cleaning position. As the catheter 1308 is withdrawn, the flap 1340 closes—either due to a bias or the suction through the catheter—to occlude the opening in the collar 1324 without having the opportunity to scrape mucus or secretions onto the distal surface of flap 1340 because of protrusion 1380 on the proximal surface of flap 1340.

As the catheter 1308 is withdrawn proximally out of the collar 1324 and past the wiper seal 1352, the distal end 1308a of the catheter is wiped by the wiper seal 1352 so that most secretions thereon are removed. The secretions that are removed by the wiper seal 1352 are then carried through the catheter 1308. It is useful to note that protrusions 1380 will scrape some of these secretions that may be suctioned using catheter 1308 during retraction.

Once the distal end 1308a of the catheter 1308 has advanced beyond the first wiper seal 1352, a bottle 1360 is attached to the lavage port 1330 and a cleaning liquid (typically sterile saline solution) is supplied through the side opening 1332 in the collar 1324. The cleaning liquid flows around the distal end 1308a of the catheter 1308, indicated by arrow 1364, and cleans those secretions which were not removed by the first wiper seal 1352 from the distal end of the catheter.

At the same time, the holes 1348 in the flap 1340 allow a small amount of air into the catheter, thereby facilitating better removal of the secretions. If desired, a make-up air valve could be disposed on the side of the adapter 1320 to allow the inflow of additional air.

Figure 10A:
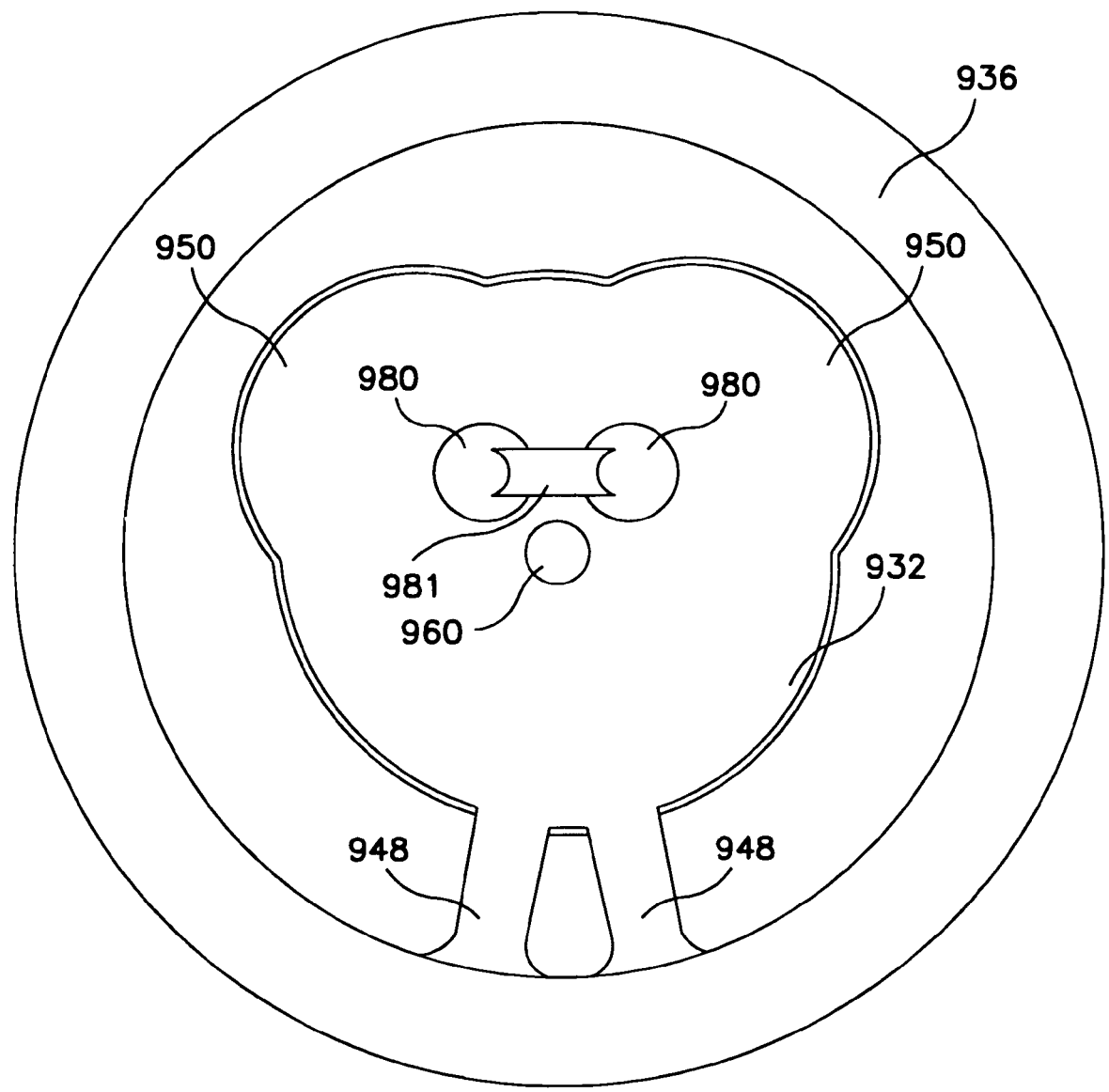
FIG. 10A shows a close-up end view of an alternate embodiment of the flap valve.

As shown in FIG. 10A, a pair of arms 948 attaches the flap 932 to the ring 936. As previously mentioned above, the arms 948 could be configured to bias the flap 932 into the closed position. The flap 932 is generally circular, but has two rounded projections 950 which extend outwardly and are spaced approximately 90 degrees apart. The projections serve two important purposes. First, even if the generally circular portion of the flap 932 were slightly smaller than the distal opening of the endotracheal tube, the projections 950 would prevent the flap from entering the endotracheal tube. Second, the projections 950 would cause the flap to align for airflow to continue to the patient without lying flat to cover any passage which might interfere with airflow to or from the patient.

Also shown in FIG. 10A is the aperture 960 that is formed in the generally circular portion of the flap 932. As shown the aperture 960 is between about 0.76 mm (0.03 inches) and about 1.02 mm (0.04 inches) in diameter. While shown as being circular or disk-shaped, those skilled in the art will appreciate, in light of the present disclosure, that other shaped apertures could also be used. As shown, a plurality of protrusions 980 may be formed on a surface of flap 932. Of note in this preferred embodiment, each protrusion 980 is integrally formed with a bridge 981 that connects each protrusion 980 to one another. This bridge 981 is designed to scrape mucus and secretions from a retracting catheter and help prevent flap 932 from deforming during translation of the catheter. Moreover, bridge 981 limits the interaction of the catheter with the proximal surface of flap 932 and strengthens flap 932 to reduce the risk of deformation of flap 932 during the translation of catheter 908 (not shown).

Figure 10B:
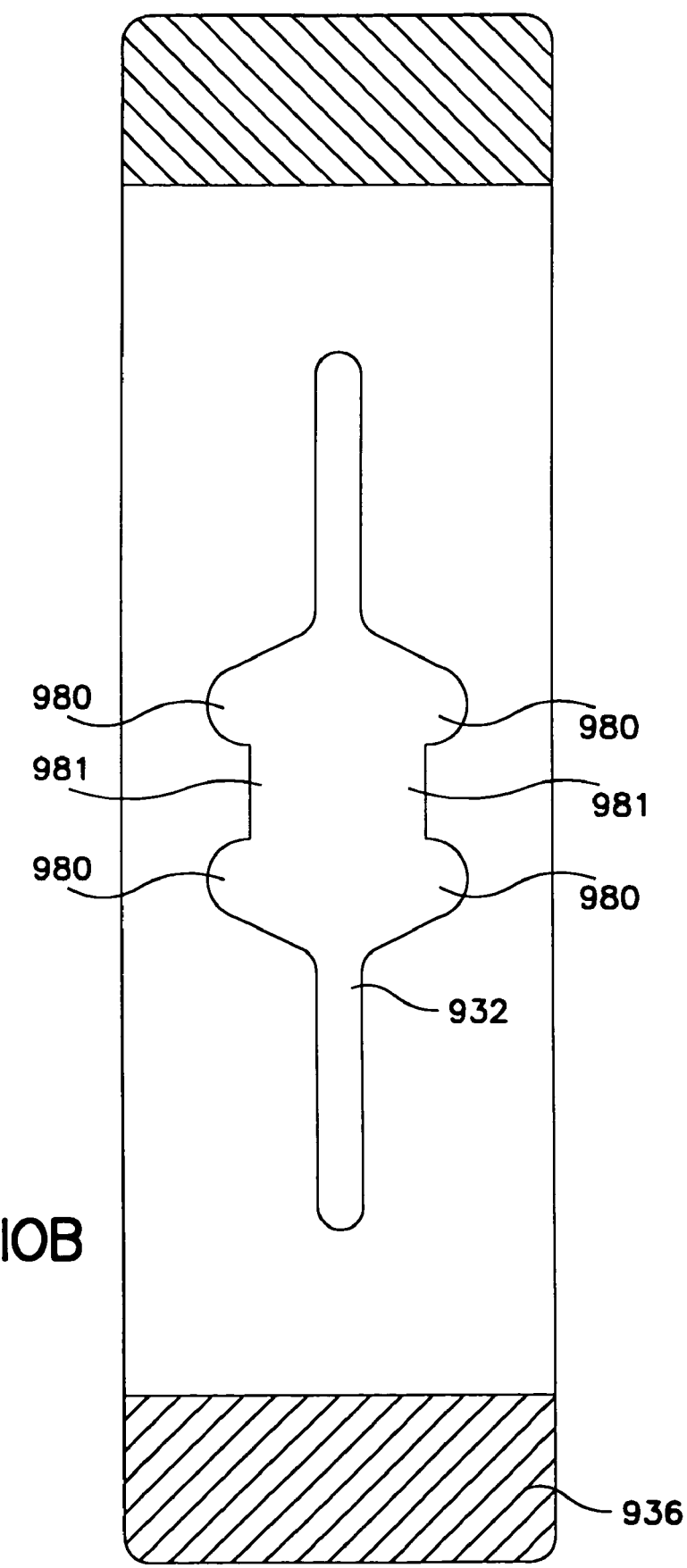
FIG. 10B shows a top cross-sectional view of an alternate embodiment of the flap valve.
Figure 10C:
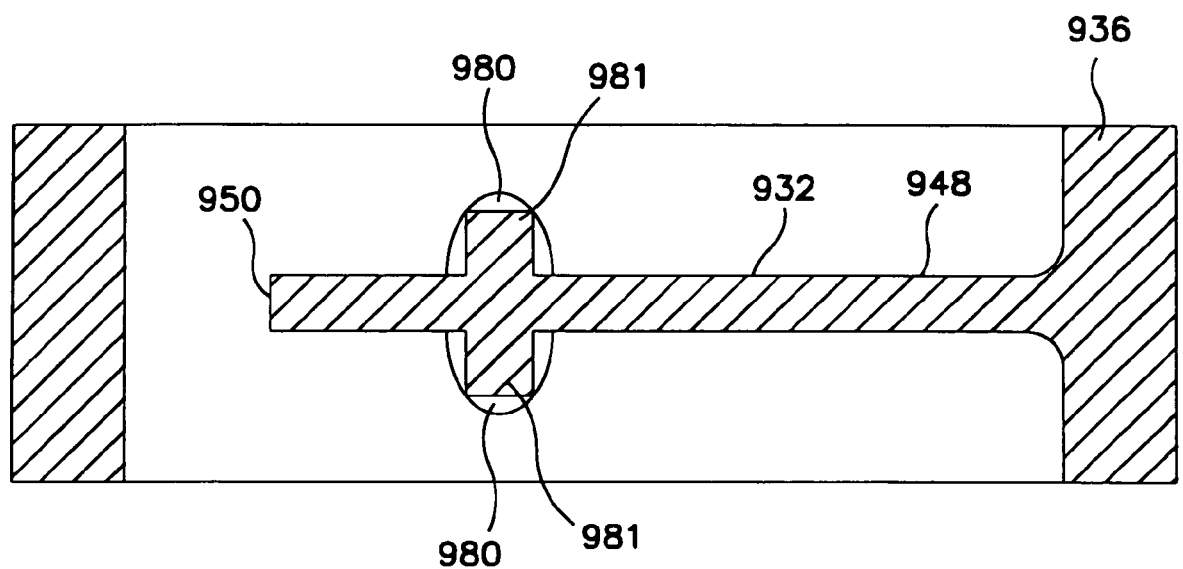
FIG. 10C shows a side cross-sectional view of an alternate embodiment of the flap valve.

Moreover, as shown in the top and side cross-sectional views of the flap 932 in FIGS. 10B and 10C, flap 932 is preferably formed with uniform and similar protrusions 980 on both the proximal and distal surfaces of flap 932. This configuration allows for more flexibility and quality control in the manufacture of assemblies comprising flap 932 or similar internal components. By forming flap 932 with identically positioned protrusions 980, and bridges 981 if included, on both the proximal and distal surfaces of flap 932, flap 932 may be incorporated into an assembly with less concern as to the orientation of flap 932 in the manufacturing process.

Those of skill in the art will recognize that the internal components such as the valve may be formed of a variety of different compositions. For instance, they may be comprised of such synthetic resins as polyurethanes, ethylene vinyl acetate copolymers, polyvinyl chlorides, polyamide/polyethers, polysilicones, polyamides, such as nylon, polyethylene, including those of the high density, low density, intermediate density and linear low density variety, ethylene α-olefin copolymers (such as ethylene propylene copolymers), polyesters, polycarbonates, acrylonitrile-butadienestyrene copolymers, polyether-polyester copolymers, and polyether polyamide copolymers are desirable. Further desirable are low pressure, relatively soft or flexible polymeric materials, such as thermoplastic polymers including thermoplastic elastomers.

Injection molded medical grade synthetic resinous materials are preferable for such internal components. Especially preferred are polyamide/polyether polyesters including those sold commercially as Pebax® by Atochem North America, Inc., Philadelphia Pa. Most preferred are the Pebax® 33 polyamide/polyether polymers, such as Pebax® 3533 SA 00 polymers. Such polymers have a Shore D, ASTM D2240, hardness of about 35, a Shore A, ASTM D2240, hardness of about 85, and a flexural modulus, ASTM D790, of about 19995500 Pa (2,900 PSI), a softening point, ASTM D1525, of approximately 73° C. (165° F.) and a melting point of between about 109° C. (228° F.) and about 154° C. (309° F.).

Further preferred is Pebax® 5533 SA 00 polyether block amide polymer characterized by a Shore D, ASTM D2240, hardness of about 55, a flexural modulus, ASTM D790, of about 165480000 Pa (24,000 PSI), a softening point, ASTM D1525, of approximately 144° C. (291° F.). And a melting point of between about 128° C. (262° F.) and about 170° C. (338° F.).

Thermoplastic elastomeric polymers which render excellent results as the internal components for use in the invention include those sold under the Monprene® name, a trademark of QST, Inc., including Monprene® MP-2870M, having a Shore A hardness, ASTM D2240, of about 70; Santoprene® name, a trademark of Advanced Elastomer Systems, including Santoprene® MP-2870M, having a Shore D hardness, ASTM D2240, of about 40; polyurethane (polyether) elastomers, such as those sold under the Pellathane™ name, a trademark of Dow Plastics, including Pellathane® 2363-80AE, having a Shore A hardness, ASTM D2240, of about 85; ethylene vinyl acetate polymer sold under the Elvax® name, a trademark of E.I. du Pont Packaging & Industrial Polymers, including Elvax® 150 (33% vinyl acetate) and Elvax® 360 (25% vinyl acetate), Elvax® 450 (18% vinyl acetate) or Elvax® 750 (9% vinyl acetate); low density polyethylene polymers, such 3447500 Pa (500 PSI); the low density polyethylenes sold under the Petrothene® trademark by Equistar Chemicals, L.P., such as Petrothene® NA 270-000 low density polyethylene polymer; polyvinyl chlorides commercially available under the Unichem™ trademark by Colorite Plastics Company, such as Unichem™ 7811G-015 polyvinyl chloride polymer, Unichem™ 8511G-015 flexible polyvinyl chloride polymer, Unichem™ 6511G-015 flexible polyvinyl chloride polymer; the styrene ethylene butylene styrene block copolymers commercially available under the Kraton™ trademark by Shell Chemical Company, such as the Kratomm™ G-7705 styrene ethylene butylene styrene block copolymer; and the density polyethylene polymers commercially available under the Tenite™ trademark by Eastman Chemical Company, such as the Tenite™ 1870A low density polyethylene polymers.

By use of these various configurations, the cleaning of the distal end of a catheter may be enhanced while minimizing or eliminating the air drawn from the ventilation circuit of the patient. Those skilled in the art will appreciate modifications that can be made without departing scope and spirit of the present invention. The appended claims are intended to cover such modifications.

What is claimed is:

1. An endotracheal catheter system comprising:
   a suction catheter having a distal end for suctioning secretions;
   a protective sleeve surrounding a proximal longitudinal portion of the catheter;
   a manifold connected to the protective sleeve for attachment to a hub of an artificial airway in fluid communication between the respiratory tract of a patient and a ventilator, said manifold having means for accommodating inspiration and expiration of respiratory gases;
   a valve connected to the manifold and pivotally moveable with respect thereto for engaging the distal end of the catheter to minimize the amount of air being drawn thereinto responsive to suction through the catheter wherein the valve comprises at least one protrusion on a surface of the valve;
   wherein the valve comprises a pivotable flap disposed to selectively separate the distal end of the catheter; and
   a means for enhancing the turbulence of the air.

* * * * *